(12) United States Patent
Lee et al.

(10) Patent No.: US 6,395,548 B1
(45) Date of Patent: May 28, 2002

(54) METHODS OF MODULATING OF ANGIOGENESIS

(75) Inventors: Mu-En Lee, Newton; Koji Maemura, Brookline; Chung-Ming Hsieh, Cambridge, all of MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/374,454

(22) Filed: Aug. 13, 1999

Related U.S. Application Data

(60) Provisional application No. 60/096,515, filed on Aug. 14, 1998.

(51) Int. Cl.$^7$ .............................. I12N 15/09; C12N 5/00; C12N 15/63; C07H 21/04
(52) U.S. Cl. ..................... 435/455; 435/320.1; 435/325; 536/23.5
(58) Field of Search ....................... 514/44, 2; 435/455, 435/320.1, 325; 536/23.1, 23.5, 24.1, 24.2, 24.5

(56) References Cited

U.S. PATENT DOCUMENTS

| | | | | |
|---|---|---|---|---|
| 5,695,963 A | * | 12/1997 | McKnight et al. | 435/69.1 |
| 5,786,171 A | | 7/1998 | Lee et al. | 435/69.1 |
| 5,843,683 A | | 12/1998 | Edery et al. | 435/7.8 |
| 5,874,241 A | | 2/1999 | Takahashi et al. | 435/69.1 |
| 5,932,541 A | | 8/1999 | Winokur et al. | 514/2 |

FOREIGN PATENT DOCUMENTS

| | | |
|---|---|---|
| WO | WO 97/00953 | 1/1997 |
| WO | WO 98/35040 | 8/1998 |

OTHER PUBLICATIONS

Verma IM and Somia N. Nature 389: 239–242., 1997.*
Crystal RG. Science 270:404–410., 1995.*
Rojanasakul Y. Advanced Drug Delivery Reviews 18:115–131, 1996.*
Sherman MI. Annals of NY Acad. Sci. 616:201–204, 1990.*
Holt J. Mol Med Today 2:184–185, 1996.*
Maemura et al (The Journal of Biological Chemistry 274:31565–31570, 1999.*
Ema et al. (1997) "A Novel bHLH–PAS Factor With Close Sequence Similarity To Hypoxia–Inducible Factor 1αRegulats THe VEGF Expression And is Potentially Involved in Lung and Vascular Development", Proc. Natl. Acad. Sci. USA, vol. 94, pp. 4273–4278.
Luo et al. (1997) "Molecular Characterization of The Murine Hif–1α Locus", Gene Expression, vol. 6, pp. 287–299.
Luo et al., "Molecular Characterization of Murine Hif–1a Locus", Gene Expression, vol. 6, pp. 287–299, 1997.
Scott et al., "Role of the Hypoxia Sensing System, Acidity and Reproduction Hormones . . . ", Int. J. Cancer, 75, 706–712 (1998).
Tian H. et al., "A Transcription Factor Selectively Expressed in Endothelial Cells", Genes Dev. 11 (1), 72–82 (1997) Accession No. U91884.
Thompson et al., "Clustal W: improving the sensitivity of progressive multiple sequence alignment through sequence . . . ", Nucleic Acids Research, 1994, vol. 22, No. 22 4673–4680.
Wang et al., "Hypoxia–inducible factor 1 is a basic–helix–loop–helix–PAS . . . ", Proc. Natl. Acad Sci. USA vol. 92, pp. 5510–5514, Jun. 1995.
Melani et al., "Inhibition of Proliferation by c–myb Antisense Oligodeoxynecleotides in Colon Adenocarcinoma Cell . . . ", Cancer Research 51, 2897–2901, Jun. 1, 1991.
Williams et al., "Introduction of foreign genes into tissues of living mice by DNA–coated microprojectiles", Chemical Reviews, vol. 90, No. 4, Jun. 1990.
Tidd D., "A Potential Role for Antisense Oligonucleotide Analogues in the Development of Oncogene Targeted Cancer Chemotherapy", Anticancer Research 10: 1169–1182 (1990).
Dolnick B., "Antisense Agents in Pharmacology", Biochemical Pharmacology, vol. 40, No. 4, pp. 671–675, 1990.
Crooke S., "Therapeutic Applications of Oligonucleotides", Annu. Rev. Pharmacol. Toxical. 1992, 32:329–76 1992.
Marasco et al., "Design, intracellular expression, and activity of a human anti–human immunodeficiency virus type 1 gp120 signle–chain antibody", Proc. Natl. Acad. Sci. USA vol. 90, pp. 7889–7893, Aug. 1993.
Marasco WA, "Intrabodies: tuning the humoral immune system outside in for intracellular immunization", Gene Therapy (1997) 4, 11–15, 1997.
Turek F., "Circadian Rhythms", Horm Res 1998; 49:109–113.
Schibler U., "New cogwheels in the clockworks", Nature, vol. 393, pp. 620–621, 1998.
Higgins et al., "Using CLUSTAL for Multiple Sequence Alignments", Methods in Enzymology, vol. 266, pp. 383–402, 1996.
Doan et al., "Antisense Oligonucleotides as Potential Antiviral and Anticancer Agents", Bull. Cancer, 76 (1989) 849–852.

* cited by examiner

*Primary Examiner*—Dave T. Nguyen
*Assistant Examiner*—Ram R. Shukla
(74) *Attorney, Agent, or Firm*—Ingrid A. Beattie; Mintz Levin

(57) ABSTRACT

A method of inhibiting angiogenesis in a mammal by administering to the mammal a compound which inhibits binding of endothelial PAS domain protein-1 to cis-acting transcription regulatory sequence in the promoter region of a gene encoding an angiogenic factor.

7 Claims, 6 Drawing Sheets

```
  1 MAAEEEAAAGGKVLREENQCIAPVVSSRVSPGTRPTAMGSFSSH-MTEFPRKRKGSDSD-      hARNT4
  1 MA------------DQRMDISSTISDFMSPGPTDLLSSSLGTS-GVDCNRKRKGSSTDY      hBMAL1b
  1 MAATTANPEMTSDVPSLGPAIASGNSGPGIQGGGAIVQRAIKRRPGLDFDDDGEG-NSKF     hARNT

59 ----------------PSQVEDGEHQVKMKAFREAHSQIEKRRRDKMNNLIEELSAMIPQC    hARNT4
 47 ----QESMDTDKDDPHGRLEYTEHQGRIKNAREAHSQIEKRRRDKMNSFIDELASLVPTC    hBMAL1b
 60 LRCDDDQMSNDKERFARSDDEQSSADKERLARENHSEIERRRRNKMTAYITELSDLVPTC    hARNT

104 NPMARKLDKLTVLRMAVQHLRSLKGLTNSYVGSNYRPSFLQDNELRHLILKTAEGFLFVV    hARNT4
103 NAMSRKLDKLTVLRMAVQHMRTLRGATNPYTEANYKPTFLSDDELKHLILRAADGFLFVV    hBMAL1b
120 SALARKPDKLTTLRMAVSHMKSLRGTGNTSTDGSYKPSFLTDQELKHLILEAADGFLFIV    hARNT

164 GCERGKILFVSKSVSKILNYDQASLTGQSLFDFLHPKDVAKVKEQLSSEDISPREKLIDA    hARNT4
163 GCDRGKILFVSESVFKILNYSQNDLIGQSLFDYLHPKDIAKVKEQLSSSDTAPRERLIDA    hBMAL1b
180 SCETGRVVYVSDSVTPVLNQPQSEWFGSTLYDQVHPDDVDKLREQLSTSENALTGRIILDL  hARNT

224 KIGLQVHSNLHAGRTRVYSGSRRSFFCRLKSCKISVKEEHGC----LPN--SKK----KE   hARNT4
223 KTGLPVKTDITPGPSRLCSGARRSFFCRMKCNRPSVKVEDKD----FPSTCSKK----KA   hBMAL1b
240 KTG-TVKKEGQQSSMRMCMGSRRSFICRMRCGSSVDPVSVNRLSFVRNRCRNGLGSVKD    hARNT

274 HRK-FYTIHCTGYLRSWPPNIVGMEEERNSKKDNSNFTCLVAIGRLQPYIVPQN-SGEIN   hARNT4
275 DRKSFCTIHSTGYLKSWPPTKMGLDEDNEPDNEGQNLSCLVAIGRLHSHVVPQPVNGEIR   hBMAL1b
299 GEPHFVVVHCTGYTKAWPPAGVSLPDDDPEAGQGSKF-CLVAIGRLQVTSSPNCTDMSNV   hARNT

332 VKPTEFITREAVNGKFVYVDQRATAILGYLPQELLGTSCYEYFHQDDHNNLTDKHKAVLQ   hARNT4
335 VKSMEYVSRHAIDGKFVFVDQRATAILAYLPQELLGTSCYEYFHQDDIGHLAECHRQVLQ   hBMAL1b
358 CQPTEFISRHNIEGIFTFVDHRCVATVGYQPQELLGKNIVEFCHPEDQQLLRDSFQQVVK   hARNT

392 SKEKILIDSYKFRAKDGSFVTLKSQWFSFTNPWTKELEYIVSVNTLV---------LGH   hARNT4
395 TREKITTNCYKFKIKDGSFITLRSRWFSFMNPWTKEVEYIVSTNTVV---------LAN   hBMAL1b
418 LKGQVLSVMFRFRSKNQEWLWMRTSSFTFQNPYSDEIEYIICTNTNVKNSSQEPRPTLSN   hARNT

442 S-E----PGEASF--------LPCSSQS--------------------SEESSR      hARNT4
445 VLE----GGDPTFP------QLTASPHSMDSML-------------------PSGEGGPK  hBMAL1b
478 TIQRPQLGPTANLPLEMGSGQLAPRQQQQQTELDMVPGRDGLASYNHSQVVQPVTTTGPE   hARNT

463 QSCM-------------------------SVPGM----------------   hARNT4
476 RTHP-----------------------------TVPGI----------------   hBMAL1b
538 HSKPLEKSDGLFAQDRDPRFSEIYHNINADQSKGISSSTVPATQQLFSQGNTFPPTPRPA   hARNT

472 ----------STGTVLGAGSIGTDIANEILDLQRLQSSSYL----------------    hARNT4
485 ----------PGGTRAGAGKIGRMIAEEIMEIHRIRGSSPS----------------    hBMAL1b
598 ENFRNSGLAPPVTIVQPSASAGQMLAQISRHSNPTQGATPTWTPTTRSGFSAQQVATQAT   hARNT

503 ----------------DDSSPTGLMKDTHTVNCRSMSNKELFPPSPSEM---GELEATRQN  hARNT4
516 ----------------SCGSSPLNITSTPPPDASSPGGKKILNGGTPDIPSSGLLSCQAQE  hBMAL1b
658 AKTRTSQFGVGSFQTPSSFSSMSLPGAPTASPGAAAYPSLTNRGSNFAPETGQTAGQFQT   hARNT

545 QSTVAVHSHEPLLSDGAQLDFDALCDN--------DDTAMAAFMNYLEAEGGLGDP---G  hARNT4
561 NPGYPYSDSSSILGENPHIGIDMIDNDQGSSSFSNDEAAMAVIMSLLEADAGLGGP---V  hBNAL1b
718 RTAEGVGVWPQWQGQOPH-HRSSSSEQHVQQPFAQQPGQPEVFQEMLSMLGDQSNSYNNE  hARNT

594 DFSDI----QWTL              hARNT4(SEQ ID NO:19)
618 DFSDL----PWPL              hBMAL1b(SEQ ID NO:21)
777 EFPDLTMFPPFSE              hARNT(SEQ ID NO:22)
```

Fig. 3A

METHODS OF MODULATING OF ANGIOGENESIS

This application claims the benefit of U.S. Provisional Application No. 60/096515, filed Aug. 14, 1998. +gi

STATEMENT AS TO FEDERALLY SPONSORED RESEARCH

This invention was made in part with funds from the Federal Government under National Institutes of Health grants HL 09008, HL 55454, HL 03194, HL 57664, GM 53249 and HL 57977.

BACKGROUND OF THE INVENTION

This invention relates to vascular therapy.

Angiogenesis results from endothelial cell proliferation induced by angiogenic factors. Angiogenic factors bind to receptors on endothelial cells which line blood vessels. This event triggers signals which cause the cells to proliferate; the proliferating endothelial cells secrete proteases which digest the basement membrane surrounding a vessel. The junctions between the endothelial cells are altered, allowing projections from the cells to pass through the space created. These outgrowths then become new blood vessels, e.g., capillaries.

Vascular endothelial cell growth factor (VEGF) and VEGF receptors (VEGF-Rs) play a role in vasculogenesis and angiogenesis. Although VEGF is secreted by a variety of cell types, including vascular smooth muscle cells, osteoblasts, fibroblasts, and macrophages, its proliferative and chemotactic activities are restricted to endothelial cells. VEGF signaling is mediated by two VEGF-Rs, the endothelial cell-specific tyrosine kinase receptors, flt-1 and KDR/flk-1. Despite its importance in VEGF signaling, the molecular mechanisms of VEGF and VEGF-R expression have not been elucidated.

SUMMARY OF THE INVENTION

The invention is based on the discovery that endothelial PAS domain protein-1 (EPAS1) binds to cis-acting regulatory sequences associated with genes encoding such angiogenic factors as VEGF and VEGF-Rs such as KDR/flk-1 and flt-1, thereby transactivating the promoters of such genes. Accordingly, the invention features a method of increasing the level of EPAS1 in a cell, e.g., an endothelial cell. An increase in the level of EPAS1 leads to increased promoter transactivation and increased transcription of genes encoding angiogenic factors which participate in the blood vessel formation.

The invention also includes a novel basic helix-loop-helix/Per-AhR-Arnt-Sim (bHLH/PAS) protein which binds to EPAS1 and forms a heterodimer which transactivates transcription of genes encoding angiogenic factors. Increasing the level of ARNT4 in a cell, e.g., an endothelial cell also leads to increased promoter transactivation and increased expression of angiogenic factors which participate in the blood vessel formation.

Angiogenic factors are proteins or polypeptides and ligands thereof that participate in the process of new blood vessel formation. For example, angiogenic factors include VEGF, VEGF-Rs, and other signalling proteins such as intracellular tyrosine kinases which participate in the angiogenic process. Preferably, the angiogenic factors are expressed in endothelial cells, e.g., VEGF, VEGF-Rs such as KDR/flk-1 or flt-1, and tyrosine kinases such as Tie2.

A method of inhibiting angiogenesis in a mammal is carried out by administering to the mammal a compound which inhibits binding of EPAS1 to cis-acting transcription regulatory DNA associated with a gene encoding an angiogenic factor. Angiogenesis is also inhibited by administering a compound which inhibits binding of EPAS1 to ARNT4, i.e., a compound which inhibits the formation of a functional heterodimer that can transactivate a promoter of gene encoding an angiogenic factor. The angiogenic factor is preferably VEGF, a VEGF-R such as KDR/flk-1 or flt-1. For example, the compound inhibits transcription of the angiogenic factor by binding to a cis-acting regulatory sequence such as the sequence 5' GCCCTACGTGCTGTCTCA 3' (SEQ ID NO:1) in VEGF promoter DNA. For example, the compound is an EPAS1 polypeptide that binds to a cis-acting regulatory sequence of a gene but fails to transactivate the promoter of the gene, e.g, a polypeptide lacking a transactivation domain (amino acids 486–690 of EPAS1).

Table 1: Transactivation Domain of Human EPAS1
EDYYTSLDNDLKIEVIEKLFAM-
DTEAKDQCSTQTDFNELDLETLAPYIP-
MDGEDFQLSPI CPEERLLAENPQSTPQHCFSAMT-
NIFQPLAPVAPHSPFLLDKFQQQLESKKTEPEHRPMS
SIFFDAGSKASLPPCCGQASTPLSSMG-
GRSNTQWPPDPPLHFGPTKWAVGDQRTEFLGAA
PLGPPVSPPHVSTFKTRSAKGFGAR (SEQ ID NO:2)

When such an EPAS1 mutant is bound to a cis-acting regulatory DNA, it prevents wild type EPAS1 binding and thereby inhibits transcription of a gene encoding an angiogenic factor (and, in turn, angiogenesis). For example, the EPAS1 polypeptide contains the N-terminal binding domain (amino acids 14–67 of EPAS1; RRKEKSRDAARCRR-SKETEVFYELAHELPLPHSVSSHLD-KASIMRLEISFLRTH; SEQ ID NO:3) more preferably the EPAS polypeptide contains amino acids 1–485 of human EPAS1. The amino acid sequence of such an EPAS1 dominant negative mutant polypeptide and DNA encoding such a mutant polypeptide is provided below.

TABLE 2

EPAS1 dominant negative mutant

| | | | | | |
|---|---|---|---|---|---|
| 1 MTADKEKKRS | SSERRKEKSR | DAARCRRSKE | TEVFYELAHE | LPLPHSVSSH | (SEQ ID NO:4) |
| 51 LDKASIMRLE | ISFLRTHKLL | SSVCSENESE | AEADQQMDNL | YLKALEGFIA | |
| 101 VVTQDGDMIF | LSENISKFMG | LTQVELTGHS | IFDFTHPCDH | EEIRENLSLK | |
| 151 NGSGFGKKSK | DMSTERDFFM | RMKCTVTNRG | RTVNLKSATW | KVLHCTGQVK | |
| 201 VYNNCPPHNS | LCGYKEPLLS | CLIIMCEPIQ | HPSHMDIPLD | SKTFLSRHSM | |
| 251 DMKFTYCDDR | ITELIGYHPE | ELLGRSAYEF | YHALDSENMT | KSHQNLCTKG | |

TABLE 2-continued
EPAS1 dominant negative mutant

301 QVVSGQYRML AKHGGYVWLE TQGTVIYNPR NLQPQCIMCV NYVLSEIEKN

351 DVVFSMDQTE SLFKPHLMAM NSIFDSSGKG AVSEKSNFLF TKLKEEPEEL

401 AQLAPTPGDA IISLDFGNQN FEESSAYGKA ILPPSQPWAT ELRSHSTQSE

451 AGSLPAFTVP QAAAPGSTTP SATSSSSSCS TPNSP

TABLE 3
DNA encoding EPAS1 Dominant Negative Mutant cctgactgcgcggggcgctcgggacctgcgcgcacctcggaccttcaccacccgcccggg  (SEQ ID NO:5)

ccgcggggagcggacgagggccacagccccccacccgccagggagcccaggtgctcggcg tctgaacgtctcaaagggccacagcgacaatgacagctgacaaggagaagaaaaggagta gctcggagaggaggaaggagaagtcccgggatgctgcgcggtgccggcggagcaaggaga cggaggtgttctatgagctggcccatgagctgcctctgccccacagtgtgagctcccatc tggacaaggcctccatcatgcgactggaaatcagcttcctgcgaacacacaagctcctct cctcagtttgctctgaaaacgagtccgaagccgaagctgaccagcagatggacaacttgt acctgaaagccttggagggtttcattgccgtggtgacccaagatggcgacatgatcttttc tgtcagaaaacatcagcaagttcatgggacttacacaggtggagctaacaggacatagta tctttgacttcactcatccctgcgaccatgaggagattcgtgagaacctgagtctcaaaa atggctctggttttgggaaaaaaagcaaagacatgtccacagagcgggacttcttcatga ggatgaagtgcacggtcaccaacagaggccgtactgtcaacctcaagtcagccacctgga aggtcttgcactgcacgggccaggtgaaagtctacaacaactgccctcctcacaatagtc tgtgtggctacaaggagcccctgctgtcctgcctcatcatcatgtgtgaaccaatccagc acccatcccacatggacatcccctggatagcaagaccttcctgagccgccacagcatgg acatgaagttcacctactgtgatgacagaatcacagaactgattggttaccaccctgagg agctgcttggccgctcagcctatgaattctaccatgcgctagactccgagaacatgacca agagtcaccagaacttgtgcaccaagggtcaggtagtaagtggccagtaccggatgctcg caaagcatgggggctacgtgtggctggagacccaggggacggtcatctacaaccctcgca acctgcagccccagtgcatcatgtgtgtcaactacgtcctgagtgagattgagaagaatg acgtggtgttctccatggaccagactgaatccctgttcaagccccacctgatggccatga acagcatctttgatagcagtggcaagggggctgtgtctgagaagagtaacttcctattca ccaagctaaaggaggagcccgaggagctggcccagctggctccaccccaggagacgcca tcatctctctggatttcgggaatcagaacttcgaggagtcctcagcctatggcaaggcca tcctgccccccgagccagccatgggccacggagttgaggagccacagcacccagagcgagg ctgggagcctgcctgccttcaccgtgccccaggcagctgccccgggcagcaccacccca gtgccaccagcagcagcagcagctgctccacgcccaatagcccttga Rather than administering EPAS1 polypeptides or ARNT4 polypeptides, the method may be carried out by administering DNA encoding such polypeptides. For example, the compound is a nucleic acid encoding an EPAS1 polypeptide lacking amino acids 486–690 of EPAS1. For example, the nucleic acid encodes a dominant negative mutant of EPAS1 which contains amino acids 1–485 of wild type EPAS1, i.e., SEQ ID NO:5.

For antisense therapy, the compound is a antisense nucleic acid molecule containing at least 10 nucleotides the sequence of which is complementary to an mRNA encoding all or part of a wild type EPAS1 polypeptide. Preferably, the compound, e.g., an antisense oligonucleotide or antisense RNA produced from an antisense template, inhibits EPAS1 expression. For example, the compound may inhibit EPAS1 expression by inhibiting translation of EPAS1 mRNA. For example, antisense therapy is carried out by administering a single stranded nucleic acid complementary at least a portion of EPAS1 MRNA to interfere with the translation of MRNA into protein, thus reducing the amount of functional EPAS1 produced in the cell. A reduction in the amount of functional transactivating EPAS1 reduces the level of transcription of angiogenic factors such as VEGF or VEGF-Rs, resulting in a decrease in new blood vessel formation.

Alternatively, the compound is an EPAS1-specific intrabody, i.e., a recombinant single chain EPAS1-specific antibody that is expressed inside a target cell, e.g., a vascular endothelial cell. Such an intrabody binds to endogenous intracellular EPAS1 and prevents it from binding to its target cis-acting regulatory sequence in the promoter region of a gene encoding an angiogenic factor such as VEGF or a VEGF-R. An ARNT4-specific intrabody is also useful to inhibit angiogenesis.

Angiogenesis contributes to the progression of atherosclerotic lesions. Thus, compounds are administered to a site of an atherosclerotic lesion in a mammal to inhibit growth of a lesion. Compounds may also be locally administered to a tumor site to reduce blood vessel formation, thereby depriving a tumor of blood supply and inhibiting tumor growth. VEGF itself is a growth factor for some tumors; the methods described above directly inhibit VEGF expression, and thus, are particularly useful for treating such tumor types.

The invention also includes an antibody which binds to EPAS1. The antibody preferably binds to the C-terminal portion of EPAS1 (e.g., a polypeptide having the amino acid of SEQ ID NO:17 or 18). The antibody is a polyclonal or monoclonal antibody which specifically binds to the EPAS1. Preferably, the antibody binds to an epitope within the C-terminal transactivation domain (SEQ ID NO:2). The invention encompasses not only an intact monoclonal antibody, but also an immunologically-active antibody fragment, e.g., a Fab or (Fab)$_2$ fragment; an engineered single chain Fv molecule; or a chimeric molecule, e.g., an antibody which contains the binding specificity of one antibody, e.g., of murine origin, and the remaining portions of another antibody, e.g., of human origin.

To promote angiogenesis in a mammal, a compound, e.g., DNA encoding EPAS1 or a functional fragment thereof, which increases expression of VEGF or a VEGF-R in an endothelial cell is administered to a mammal, e.g., an adult mammal which has been identified as being in need of therapy to promote angiogenesis such as a patient suffering from peripheral vascular disease. A functional fragment of EPAS1 is one which binds to DNA in the promoter region of a gene encoding an angiogenic factor.

The invention also features an EPAS-binding element, ARNT4 and a nucleic acid which encodes ARNT4. For example, the nucleic acid includes a sequence which encodes the amino acid sequence a naturally-occurring human ARNT4 (SEQ ID NO:19). The DNA may encode a naturally-occurring mammalian ARNT4 polypeptide such as a human, rat, mouse, guinea pig, hamster, dog, cat, pig, cow, goat, sheep, horse, monkey, or ape ARNT4. Preferably, the DNA encodes a human ARNT4 polypeptide, e.g., a polypeptide which contains part or all of the amino acid sequence of SEQ ID NO:19. The invention includes degenerate variants of the human cDNA (SEQ ID NO:20). The DNA contains a nucleotide sequence having at least 50% sequence identity to SEQ ID NO:20. For example, the DNA contains a sequence which encodes a human ARNT4 polypeptide, such as the coding sequence of SEQ ID NO:20 (nucleotides 220 to 2025 of SEQ ID NO:20). The DNA contains a strand which hybridizes at high stringency to a strand of DNA having the sequence of SEQ ID NO:20, or the complement thereof. The DNA has at least 50% sequence identity to SEQ ID NO:20 and encodes a polypeptide having the biological activity of a ARNT4 polypeptide, e.g. the ability to bind to EPAS1 to form a heterodimer. Preferably, the DNA has at least 75% identity, more preferably 85% identity, more preferably 90% identity, more preferably 95% identity, more preferably 99% identity, and most preferably 100% identity to the coding sequence of SEQ ID NO:20.

Nucleotide and amino acid comparisons are carried out using the CLUSTAL W sequence alignment system with (Thompson et al., 1994, Nucleic Acids Research 22:4673–4680 or http://www.infobiogen.fr/docs/ClustalW/clustalw.html). Amino acid sequences were compared using CLUSTAL W with the PAM250 residue weight table. "Per cent sequence identity", as that term is used herein, is determined using the CLUSTAL W sequence alignment system referenced above, with the parameters described herein. In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Hybridization is carried out using standard techniques, such as those described in Ausubel et al. (*Current Protocols in Molecular Biology*, John Wiley & Sons, 1989). "High stringency" refers to nucleic acid hybridization and wash conditions characterized by high temperature and low salt concentration: wash conditions of 65° C. at a salt concentration of 0.1×SSC. "Low" to "moderate" stringency denotes DNA hybridization and wash conditions characterized by low temperature and high salt concentration: wash conditions of less than 60° C. at a salt concentration of 1.0×SSC. For example, high stringency conditions include hybridization at 42° C., and 50% formamide; a first wash at 65° C., 2×SSC, and 1% SDS; followed by a second wash at 65° C. and 0.1%×SSC. Lower stringency conditions suitable for detecting DNA sequences having about 50% sequence identity to an ARNT4 gene are detected by, for example, hybridization at 42° C. in the absence of formamide; a first wash at 42° C., 6×SSC, and 1% SDS; and a second wash at 50° C., 6×SSC, and 1% SDS.

A vector containing an ARNT4-encoding DNA is also within the invention. Preferably the DNA which includes an ARNT4-encoding DNA is less than 5 kilobases in length; more preferably, the DNA is less than 4 kilobases in length, more preferably the DNA is less than 3 kilobases in length, and most preferably the DNA is approximately 2 kilobases or less in length. The invention also provides a method of directing cardiac-specific or smooth muscle cell-specific expression of a protein by introducing into a cell an isolated DNA containing a sequence encoding the protein operably linked to the tissue-specific promoter. A cell containing the DNA or vector of the invention is also within the invention.

By "substantially pure DNA" is meant DNA that has a naturally-occurring sequence or that is free of the genes which, in the naturally-occurring genome of the organism from which the DNA of the invention is derived, flank the ARNT4 gene. The term therefore includes, for example, a recombinant DNA which is incorporated into a vector, into an autonomously replicating plasmid or virus, or into the genomic DNA of a procaryote or eucaryote at a site other than its natural site; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

Also within the invention is a substantially pure human ARNT4 polypeptide. The term ARNT4 polypeptide includes a polypeptide having the amino acid sequence and length of the naturally-occurring ARNT4 as well as fragments of the full-length naturally-occurring ARNT4. The polypeptide contains the amino acid sequence of SEQ ID NO:19. Preferably the polypeptide contains an amino acid sequence which is at least 50% identical to SEQ ID NO:19. Preferably, the amino acid sequence has at least 75% identity, more preferably 85% identity, more preferably 90% identity, more preferably 95% identity, more preferably 99% identity, and most preferably 100% identity to the amino acid sequence of SEQ ID NO:19. For example, the ARNT4 polypeptide may have the amino acid sequence of the naturally-occurring human polypeptide, e.g., a polypeptide which includes the amino acid sequence of SEQ ID NO:19. The invention also encompasses a polypeptide with the amino acid sequence of a segment of SEQ ID NO: 17 which spans residues 75 to 128, inclusive, or a segment spanning residues 155 to 207, inclusive, of SEQ ID NO:19, or a segment spanning residues 232 to 384 of SEQ ID NO:19. Preferably, such a polypeptide has a biological activity of a naturally-occurring ARNT4 polypeptide, e.g, heterodimer formation with EPAS1 or the ability to transactivate transcription under the control of a VEGF promoter.

A substantially pure ARNT4 polypeptide is obtained by extraction from a natural source; by expression of a recombinant nucleic acid encoding a ARNT4 polypeptide; or by chemically synthesizing the protein. A polypeptide or protein is substantially pure when it is separated from those contaminants which accompany it in its natural state (proteins and other naturally-occurring organic molecules). Typically, the polypeptide is substantially pure when it constitutes at least 60%, by weight, of the protein in the preparation. Preferably, the protein in the preparation is at least 75%, more preferably at least 90%, and most preferably at least 99%, by weight, ARNT4. Purity is measured by any appropriate method, e.g., column chromatography, polyacrylamide gel electrophoresis, or HPLC analysis. Accordingly, substantially pure polypeptides include recombinant polypeptides derived from a eucaryote but produced in E. coli or another procaryote, or in a eucaryote other than that from which the polypeptide was originally derived.

The invention also includes a transgenic non-human mammal, the germ cells and somatic cells of which contain a null mutation in a gene encoding an ARNT4 polypeptide. For example, the null mutation is a deletion of part or all of an exon of ARNT4. Preferably, the mammal is a rodent such as a mouse. An antibody which specifically binds to a ARNT4 polypeptide is also within the invention.

Angiogenesis is inhibited by administering to a mammal a compound which inhibits binding of EPAS1 to ARNT4 such as an ARNT4 polypeptide. For example, the compound is a polypeptide or peptide mimetic which contains the amino acid sequence of residues 75 to 128, inclusive, of SEQ ID NO:19, the amino acid sequence of residues 155 to 207, inclusive, of SEQ ID NO:19, or a the amino acid sequence of residues 232 to 384 of SEQ ID NO:19.

Other features and advantages of the invention will be apparent from the following detailed description and from the claims.

DETAILED DESCRIPTION

The drawings will first be describe.

DRAWINGS

FIG. 1A is a bar graph showing dose-dependent transactivation of KDR/flk-1 promoter by EPAS1. EPAS1 expression plasmid phEP-1 (0–6 μg), pcDNA3 (6–0 μg), and KDR/flk-1 reporter pGL2-4 kb+296 (1 μg) were transfected into BAEC.

FIG. 1B is a bar graph showing that deletion of EPAS1 C-terminal region abolishes its ability to transactivate the KDR/flk-1 promoter. Expression plasmids (6 μg each) and pGL2-4 kb+296 (1 μg) were cotransfected into BAEC. For all constructs in FIGS. 1A–1B, the plasmid pCMV-βGAL was cotransfected to correct for differences in transfection efficiency. In both FIGS. 1A and 1B, liciferase activity and β-galactosidase activity were measured, and normalized luciferase activity was calculated as described below. The "fold induction" represents the ratio (mean±SE) of normalized luciferase activity in cells transferred with expression plasmid to that in cells transfected with empty vector (pcDNA3), phEP-1 represents EPAS1 expression plasmid, and phEP-1 ΔCT represents an expression plasmid encoding a truncated form of EPAS1 lacking its 180 C-terminal amino acids.

FIG. 2A is a bar graph showing transactivation of the KDR/flk-1 promoter by EPAS1 but not by HIF 1α (another member of the PAS family of transcription factors). Expression plasmids (6 μg each) and KDR/flk-1 reporter pGL2-4 kb+296 (1 μg) were cotransfected into the cell types indicated. In both FIGS. 2A and 2B, phEP-1 represents EPAS1 expression plasmid, and phEP-1AS represents EPAS1 antisense plasmid.

FIG. 2B is a bar graph showing transactivation of a VEGF promoter by EPAS1 and HIF-1α. Expression plasmids (6 μg each) and VEGF reporter pVR47/CAT (1 μg) were cotransfected into the cell types indicated. For all constructs in FIGS. 2A–2B, the plasmid pCMV-βGAL was cotransfected to correct for differences in transfection efficiency. The "fold induction" represents the ratio (mean±SE) of normalized luciferase or CAT activity in cells transfected with expression plasmid to that in cells transfected with empty vector (pcDNA3).

FIG. 3A is a diagram showing an alignment of the amino acid sequence of human ARNT4 with human BMAL1b and human ARNT.

DESCRIPTION OF THE PREFERRED EMBODIMENTS

Figure 1A:
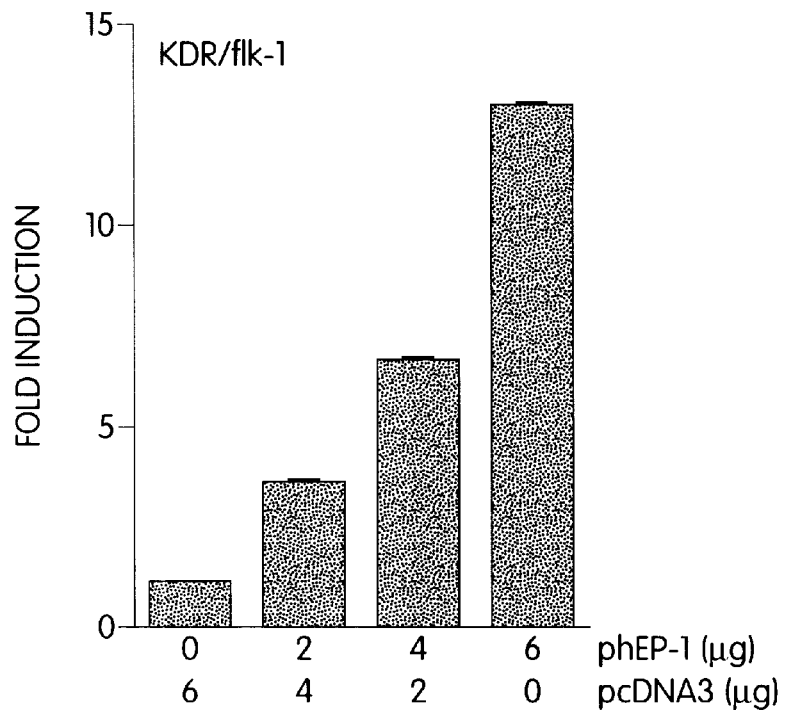

EPAS1 is a member of the transcription factor family characterized by a basic helix-loop-helix (bHLH) domain and a (Per-AhR-Arnt-Sim) PAS domain composed of two imperfect repeats. Table 4 shows the amino acid sequence of human wild type EPAS1.

TABLE 4

Amino acid sequence of human EPAS1

MTADKEKKRSSSERRKEKSRDAARCRRSKETEVFYELAHELPLPHSVSSHLDKASIMRLE (SEQ ID NO:6)
ISFLRTHKLLSSVCSENESEAEADQQMDNLYLKALEGFIAVVTQDGDMIFLSENISKFMG
LTQVELTGHSIFDFTHPCDHEEIRENLSLKNGSGFGKKSKDMSTERDFFMRMKCTVTNRG
RTVNLKSATWKVLHCTGQVKVYNNCPPHNSLCGYKEPLLSCLIIMCEPIQHPSHMDIPLD
SKTFLSRHSMDMKFTYCDDRITELIGYHPEELLGRSAYEFYHALDSENMTKSHQNLCTKG
QVVSGQYRMLAKHGGYVWLETQGTVIYNPRNLQPQCIMCVNYVLSEIEKNDVVFSMDQTE
SLFKPHLMAMNSIFDSSGKGAVSEKSNFLFTKLKEEPEELAQLAPTPGDAIISLDFGNQN
FEESSAYGKAILPPSQPWATELRSHSTQSEAGSLPAFTVPQAAAPGSTTPSATSSSSSCS
TPNSP<u>EDYYTSLDNDLKIEVIEKLFAMDTEAKDQCSTQTDFNELDLETLAPYIPMDGEDF</u>
<u>QLSPICPEERLLAENPQSTPQHCFSAMTNIFQPLAPVAPHSPFLLDKFQQQLESKKTEPE</u>
<u>HRPMSSIFFDAGSKASLPPCCGQASTPLSSMGGRSNTQWPPDPPLHFGPTKWAVGDQRTE</u>
<u>FLGAAPLGPPVSPPHVSTFKTRSAKGFGAR</u>GPDVLSPAMVALSNKLKLKRQLEYEEQAFQ
DLSGGDPPGGSTSHLMWKRMKNLRGGSCPLMPDKPLSANVPNDKFTQNPMRGLGHPLRHL
PLPQPPSAISPGENSKSRFPPQCYATQYQDYSLSSAHKVSGMASRLLGPSFESYLLPELT
RYDCEVNVPVLGSSTLLQGGDLLRALDQAT

The N-terminal bHLH domain (which plays a role in DNA binding) and the C-terminal transactivation domain are highlighted (in bold and underlined type, respectively).

Table 5 shows the nucleotide sequence DNA encoding human wild type EPAS1. Nucleotides encoding the first amino acid of EPAS1 are underlined.

TABLE 5

Nucleotide sequence of human EPAS1 CDNA

```
   1 cctgactgcg cggggcgctc gggacctgcg cgcacctcgg accttcacca cccgcccggg(SEQ ID NO:7)
  61 ccgcggggag cggacgaggg ccacagcccc ccacccgcca gggagcccag gtgctcggcg
 121 tctgaacgtc tcaaagggcc acagcgacaa tgacagctga caaggagaag aaaaggagta
 181 gctcggagag gaggaaggag aagtcccggg atgctgcgcg gtgccggcgg agcaaggaga
 241 cggaggtgtt ctatgagctg gcccatgagc tgcctctgcc ccacagtgtg agctcccatc
 301 tggacaaggc ctccatcatg cgactggaaa tcagcttcct gcgaacacac aagctcctct
 361 cctcagtttg ctctgaaaac gagtccgaag ccgaagctga ccagcagatg gacaacttgt
 421 acctgaaagc cttggagggt tcattgccg tggtgaccca agatggcgac atgatcttc
 481 tgtcagaaaa catcagcaag ttcatgggac ttacacaggt ggagctaaca ggacatagta
 541 tctttgactt cactcatccc tgcgaccatg aggagattcg tgagaacctg agtctcaaaa
 601 atggctctgg ttttgggaaa aaagcaaag acatgtccac agagcgggac ttcttcatga
 661 ggatgaagtg cacggtcacc aacagaggcc gtactgtcaa cctcaagtca gccacctgga
 721 aggtcttgca ctgcacgggc caggtgaaag tctacaacaa ctgccctcct cacaatagtc
 781 tgtgtggcta caaggagccc ctgctgtcct gcctcatcat catgtgtgaa ccaatccagc
 841 acccatccca catggacatc ccctggata gcaagacctt cctgagccgc cacagcatgg
 901 acatgaagtt cacctactgt gatgacagaa tcacagaact gattggttac caccctgagg
 961 agctgcttgg acgctcagcc tatgaattct accatgcgct agactccgag aacatgacca
1021 agagtcacca gaacttgtgc accaagggtc aggtagtaag tggccagtac cggatgctcg
```

TABLE 5-continued

Nucleotide sequence of human EPAS1 CDNA

```
1081 caaagcatgg gggctacgtg tggctggaga cccaggggac ggtcatctac aaccctcgca 1141 acctgcagcc ccagtgcatc atgtgtgtca actacgtcct gagtgagatt gagaagaatg 1201 acgtggtgtt ctccatggac cagactgaat ccctgttcaa gccccacctg atggccatga 1261 acagcatctt tgatagcagt ggcaaggggg ctgtgtctga gaagagtaac ttcctattca 1321 ccaagctaaa ggaggagccc gaggagctgg cccagctggc tcccacccca ggagacgcca 1381 tcatctctct ggatttcggg aatcagaact tcgaggagtc ctcagcctat ggcaaggcca 1441 tcctgccccc gagccagcca tgggccacgg agttgaggag ccacagcacc cagagcgagg 1501 ctgggagcct gcctgccttc accgtgcccc aggcagctgc cccgggcagc accacccca 1561 gtgccaccag cagcagcagc agctgctcca cgcccaatag ccctgaagac tattacacat 1621 ctttggataa cgacctgaag attgaagtga ttgagaagct cttcgccatg gacacagagg 1681 ccaaggacca atgcagtacc cagacggatt tcaatgagct ggacttggag acactggcac 1741 cctatatccc catggacggg gaagacttcc agctaagccc catctgcccc gaggagcggc 1801 tcttggcgga gaacccacag tccaccccc agcactgctt cagtgccatg acaaacatct 1861 tccagccact ggcccctgta gccccgcaca gtcccttcct cctggacaag tttcagcagc 1921 agctggagag caagaagaca gagcccgagc accggcccat gtcctccatc ttctttgatg 1981 ccggaagcaa agcatccctg ccaccgtgct gtggccaggc cagcacccct ctctcttcca 2041 tgggggcag atccaatacc cagtggcccc cagatccacc attacatttt gggcccacaa 2101 agtgggccgt cggggatcag cgcacagagt tcttgggagc agcgccgttg gggcccctg 2161 tctctccacc ccatgtctcc accttcaaga caaggtctgc aaagggtttt ggggctcgag 2221 gcccagacgt gctgagtccg gccatggtag ccctctccaa caagctgaag ctgaaycgac 2281 agctggagta tgaagagcaa gccttccagg acctgagcgg gggggaccca cctggtggca 2341 gcacctcaca tttgatgtgg aaacggatga agaacctcag gggtgggagc tgccctttga 2401 tgccggacaa gccactgagc gcaaatgtac ccaatgataa gttcacccaa aacccatga 2461 ggggcctggg ccatccctg agacatctgc cgctgccaca gcctccatct gccatcagtc 2521 ccggggagaa cagcaagagc aggttcccc cacagtgcta cgccacccag taccaggact 2581 acagcctgtc gtcagcccac aaggtgtcag gcatggcaag ccggctgctc gggccctcat 2641 ttgagtccta cctgctgccc gaactgacca gatatgactg tgaggtgaac gtgcccgtgc 2701 tgggaagctc cacgctcctg caaggagggg acctcctcag agccctggac caggccacct 2761 gagccaggcc ttctacctgg gcagcacctc tgccgacgcc gtcccaccag cttcaccc
```

Hypoxia inducible factor-1α (HIF-1α) is another member of the PAS family to which EPAS1 belongs. Transcription factors of this family use the bHLH and PAS domains to form heterodimers that subsequently bind to target genes and regulate important biological processes.

EPAS1 plays a role in the regulation of angiogenic factors such as VEGF, VEGF-R such as KDR/flk-1 and flt-1, and Tie2. EPAS1, a nuclear protein with a basic helix-loop-helix (bHLH)/PAS domain, is expressed preferentially in endothelial cells. EPAS1 transcription factor or DNA encoding all or part of EPAS1 (e.g., a fragment containing the C-terminal activation domain) is administered to individuals to promote angiogenesis. To inhibit angiogenesis, EPAS1 antisense sequences are administered to cells to decrease intracellular production of EPAS1 gene product. Administration of DNA encoding an EPAS1-specific antibody (e.g., EPAS1 intrabodies) or EPAS1 dominant negative mutants can also be administered cells to inhibit EPAS1 function, e.g., by inhibiting binding of EPAS1 to cis-acting regulatory sequences of VEGF, VEGF-R, or Tie2 genes or by inhibiting EPAS1 transactivation of gene transcription. By regulating transcription of VEGF, VEGF-Rs, and Tie2, EPAS1 is useful to modulate vasculogenesis and angiogenesis.

Production of ARNT4-Specific Antibodies

Anti-ARNT4 antibodies are obtained by techniques well known in the art. Such antibodies can be polyclonal or monoclonal. Polyclonal antibodies are obtained, for example, by the methods described in Ghose et al., Methods in Enzymology, Vol. 93, 326–327, 1983. For example, a ARNT4 polypeptide, or an antigenic fragment thereof, can be used as an immunogen to stimulate the production of ARNT4-reactive polyclonal antibodies in the antisera of animals such as rabbits, goats, sheep, or rodents. Antigenic polypeptides useful as immunogens include polypeptides which contain a bHLH domain/PAS domain.

Monoclonal antibodies are obtained by standard techniques such as those described by Milstein and Kohler in Nature, 256:495–97, 1975, or as modified by Gerhard, Monoclonal Antibodies, Plenum Press, 1980, pages 370–371. Hybridomas are screened to identify those producing antibodies that are highly specific for an ARNT4 polypeptide. Preferably, the antibody will have an affinity of at least about $10^8$ liters/mole and more preferably, an affinity of at least about $10^9$ liters/mole.

ARNT4-Deficient Mice

To further investigate the role of ARNT4 in vivo, ARNT4 knockout mice (ARNT4-deficient mice) are generated by homologous recombination. A gene targeting construct for generating ARNT4-deficient mice is made using a targeted gene deletion strategy using standard methods. The deletion in the ARNT4 gene renders the ARNT4 polypeptide non-functional. The linearized targeting construct is transfected into murine D3 embryonic stem (ES) cells, and a clone with the correct homologous recombination (yielding the appropriately disrupted ARNT4 gene) is injected into blastocysts and used to generate ARNT4-deficient mice.

Activation of the KDR/flk-1 Promoter by EPAS1 EPAS1 and KDR/flk-1 transcripts were found to colocalize in vascular endothelial cells in mouse embryonic and adult tissue. To study the expression of EPAS1 relative to KDR/flk-1, a plasmid containing 4.0 kb of human KDR/flk-1 5'-flanking sequence linked to the luciferase reporter gene and a second vector containing DNA encoding either EPAS1 or another bHLH-PAS domain transcription factor HIF-1α were cotransfected into bovine aortic endothelial cells (BAEC). EPAS1 but not HIF-1α markedly increased KDR/flk-1 promoter activity in a dose-dependent manner, and this induction of the KDR/flk-1 promoter by EPAS1 occurred preferentially in endothelial cells. In contrast, both EPAS1 and HIF-1α activated the VEGF promoter in a non-endothelial cell-specific manner. This is the first demonstration of transactivation of the KDR/flk-1 promoter by EPAS1. By regulating transcription of KDR/flk-1 and VEGF, EPAS1 plays an important role in regulating vasculogenesis and angiogenesis.

Cell Culture

BAEC were isolated and cultured in DME supplemented with 10% FCS (HyClone, Logan, UT) and antibiotics according to known procedures. BAEC were passed every 3–5 days, and cells from passages 5–7 were used for the transfection experiments. The following cell lines were obtained from the American Type Culture Collection (ATCC) and were cultured in the same medium as BAEC: HeLa cells (human epidermoid carcinoma cells; ATCC #CRL7396 and NIH 3T3 cells (mouse fibroblasts; ATCC #CRL1888).

RNA Isolation and Northern Analysis

Total RNA was isolated from mouse organs by guanidinium isothiocyanate extraction and centrifugation through cesium chloride according to standard protocols. Total RNA (10 μg) was fractionated on a 1.3% formaldehyde-agarose gel and transferred to Nitropure filters (MSI, Westborough, Mass.). The filters were then hybridized with $^{32}$P-labeled, randomly primed cDNA probes for 1 h at 68° C. in Quick-hyb solution (Stratagene, La Jolla, Calif.). The hybridized filters were washed in 30 mM NaCl, 3 mM sodium citrate, and 0.1% sodium dodecyl sulfate at 55° C. and autoradiographed for 20 h on Kodak XAR film at −80° C. To correct for differences in RNA loading, the filters were rehybridized with a radiolabeled ribosomal 18S-specific oligonucleotide. A 1.8 kb AccI-AccI fragment of mouse EPAS1 (GENBANK Accession # U81983) was used as a probe. The 667 (382–1086) bp mouse KDR/flk-1 cDNA fragment was amplified by the reverse transcriptase PCR by using mouse lung total RNA. The forward (5' GAACTTGGAT-GCTCTTTGGAAA 3'; SEQ ID NO:8) and reverse (5' CACTTGCTGGCATCATAAGGC 3'; SEQ ID NO:9) primers were used to generate PCR fragments that were subcloned into to a pCR 2.1 vector (Invitrogen, Carlsbad, Calif.). Nucleotide sequence authenticity was confirmed by the dideoxy chain termination method.

In Situ Hybridization

To generate probes for in situ hybridization, a 316 (771–1086) bp mouse EPAS1 cDNA and a 342 (2346–2687) bp mouse KDR/flk-1 cDNA from mouse lung total RNA was amplified by reverse transcriptase PCR with the following primers: EPAS1, forward 5' CATCATGTGTGAGC-CAATCCA 3' (SEQ ID NO:10) and reverse 5' GTTGTA-GATGACCGTCCCCTG 3' (SEQ ID NO:11) KDR/flk-1, forward 5' TGTACTGAGAGATGGGAACCG 3' (SEQ ID NO:12) and reverse 5' CACTTGCTGGCATCATAAGGC 3' (SEQ ID NO:13). PCR fragments were subcloned into the pCR 2.1 vector in both orientations and the authenticity of the sequences was confirmed.

Slides of E9 mouse sections were purchased from Novagen (Madison, Wis.). E12 mice and various adult mouse organs were fixed in 4% paraformaldehyde, dehydrated, and embedded in paraffin. Tissue sections (6 μm thick) were hybridized with a $^{35}$S-UTP-labeled antisense cRNA probe synthesized with the T7 RNA polymerase from linearized plasmids containing appropriate cDNA fragments using standard techniques. As a negative control, tissue sections were also hybridized with $^{35}$S-UTP-labeled sense cRNA probes. After hybridization the tissue sections were washed, and the dried tissue sections were then dipped into Kodak NTB2 emulsion (Eastman Kodak) and exposed for 10–15 days at 4° C. The sections were counterstained with hematoxylin and eosin.

Construction of Plasmids pGL2-Basic and pGL2-Control contained the firefly luciferase reporter gene (Promega, Madison, Wis.). pGL2-Basic had no promoter, whereas pGL2-Control contained the SV40 promoter and enhancer. The pGL2–4 kb+296 reporter plasmid was constructed by inserting the human KDR/flk-1 promoter from −4 kb to +296 into pGL2-Basic. pVR47/CAT, which contains the human VEGF promoter from −2362 to +61 and the chloramphenicol acetyltransferase (CAT) reporter gene sequence, was also constructed using standard techniques.

The plasmid phEP-1AS was made by cloning the antisense EPAS1 cDNA into pcDNA3. phEP-1ΔCT, containing a C-terminal deletion mutant of the EPAS1 cDNA, was generated by subcloning a BamHI-XhoI restriction fragment encoding human EPAS1 amino acids 1–690 into pcDNA3. To generate phHIF-1α, a 2622 bp cDNA fragment containing the entire open reading frame of human HIF-1α was amplified using human leukocyte total RNA and pfu DNA polymerase (Stratagene, La Jolla, Calif.). The sequences of the forward (5' GTGAAGACATCGCGGGGACC 3'; SEQ ID NO:14) and reverse (5' GTTTGTGCAGTATTGTAGC-CAGG 3'; SEQ ID NO:15) primers were based on human HIF-1α cDNA (Wang et al., 1995, Proc. Natl. Acad. Sci.

USA. 92:5510–5514). The PCR fragment was then cloned into pcDNA3, and the sequence was confirmed. Expression of phEP-1, phEP-1ΔCT, and phHIF-1α was confirmed by in vitro transcription and translation in the TNT-coupled reticulocyte lysate system (Promega, Madison, Wis.) according to the manufacturer's instructions.

Transient Transfection Assays

Cells were transfected with 1 μg of reporter construct and 6 μg of expression construct by the standard calcium phosphate method. To correct for variability in transfection efficiency against β-galactosidase, 1 μg of pCMV-βGAL was cotransfected in all experiments. Cell extracts were prepared 48 h after transfection by a detergent lysis method (Promega, Madison, Wis.). Luciferase activity was measured in duplicate for all samples with an EC&G Autolumat 953 (Gaithersburg, Md. luminometer by the Promega luciferase assay. CAT activity was assayed by a two-phase fluor diffusion method. β-galactosidase activity was assayed using standard methods. The ratio of luciferase or CAT activity to β-galactosidase activity in each sample served as a measure of normalized luciferase or CAT activity. Each construct was transfected at least four times, and each transfection was done in triplicate. Data for each construct are presented as the mean ±SE.

Statistics

Comparisons between groups were made by a factorial analysis of variance followed by Fisher's least significant difference test when appropriate. Statistical significance was accepted at $p<0.05$.

Tissue Distribution of EPAS1 and KDR/flk-1 in Adult Mice

Northern blot analysis was performed with RNA prepared from various adult mouse tissues. EPAS1 mRNA was abundant in the lung, heart, and aorta, organs known to be rich in vascular endothelial cells. When the same blot was hybridized to a mouse KDR/flk-1 probe, the expression pattern of KDR/flk-1 was identical to that of EPAS1. In situ hybridization was performed using an antisense mouse EPAS1 probe to determine which cells in the aorta expressed EPAS1. The EPAS1 message localized to the luminal layer, and the antisense EPAS1 probe but not the sense EPAS1 probe hybridized to the endothelial cells of the aorta.

Tissue Distribution of EPAS1 and KDR/flk-1 in Developing Mouse Embryos

To characterize the temporal and spatial patterns of EPAS1 and KDR/flk-1 expression in developing mouse embryos, in situ hybridization was performed with EPAS1 and KDR/flk-1 probes. In embryonic-day (E)9 mice, EPAS1 mRNA was visible in the dorsal aorta, the endocardium of the developing outflow tract, the ventricle, and the perineural vascular plexus. KDR/flk-1 mRNA was expressed similarly in the same organs. At the E9 stage of development, the mouse aorta is composed mainly of a single layer of endothelial cells. Both EPAS1 and KDR/flk-1 were expressed in endothelial cells of the aorta and other organs. At E12.5, EPAS1 MRNA was visible in the intervertebral blood vessels, heart, vascular plexuses in the meninges surrounding both the spinal cord and the brain, and choroid plexus. The distribution of KDR/flk-1 mRNA at E12.5 was strikingly similar. The EPAS1 and KDR/flk-1 mRNAs were both detected in endothelial cells of the blood vessels at higher magnification as well.

Transactivation of the KDR/flk-1 Promoter by EPAS1 in a Dose Dependent Manner

The colocalization of EPAS1 and KDR/flk-1 indicates that EPAS1 is important in regulating KDR/flk-1 expression. To test the role of EPAS1 in regulation of protein expression, a human EPAS1 expression plasmid (phEP-1) and a reporter plasmid (pGL2-4 kb+296) containing approximately 4.0 kb of the human KDR/flk-1 5'-flanking sequence linked to a luciferase reporter gene were cotransfected into BAEC. EPAS1 increased KDR/flk-1 promoter activity in a dose-dependent manner (FIG. 1A). As little as 2 μg of EPAS1 expression vector phEP-1 increased the promoter activity of KDR/flk-1 by 3-fold, and 6 μg of the EPAS1 vector increased luciferase activity by 12.9-fold. Upregulation of KDR/flk-1 promoter activity by EPAS1 was specific, since cotransfection of the EPAS1 expression vector had no effect on the activity of pGL2-Control vector driven by the potent SV40 promoter and enhancer.

Figure 1B:
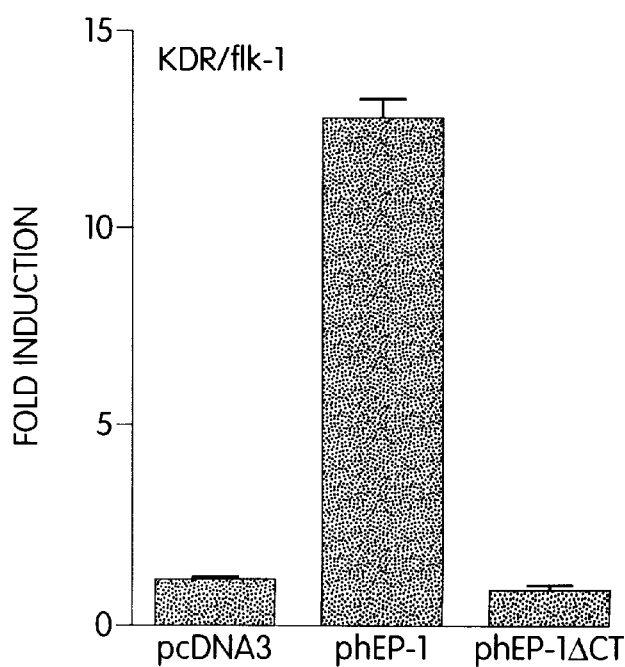

To identify the EPAS1 domain which participates in transactivation of the KDR/flk-1 promoter, plasmid phEP-1ΔCT was constructed to express a truncated form of EPAS1 lacking its 180 C-terminal amino acids. Deletion of the 180 C-terminal amino acids of EPAS1 completely abolished its ability to transactivate the KDR/flk-1 promoter (FIG. 1B). These data indicate that the 180 C-terminal amino acids of EPAS1 are necessary for transactivation of the KDR/flk-1 promoter.

These data indicate that induction of the MRNA for KDR/flk-1 colocalizes with that of the mRNA for EPAS1 in vascular endothelial cells from fetal as well as adult mice. EPAS1 also transactivates the promoter of Tie2, which, like KDR/flk-1, is an endothelial cell-specific tyrosine kinase. Expression of Tie2 in endothelial cells is high during fetal development but barely detectable in adulthood. In contrast, expression of EPAS1 in endothelial cells is high in fetuses as well as adults. Thus, the target gene for EPAS1 in adults is a VEGF-R such as KDR/flk-1 or flt-1 (as well as VEGF) as evidenced by the data showing that EPAS1 markedly induces KDR/flk-1 promoter activity.

Figure 2A:
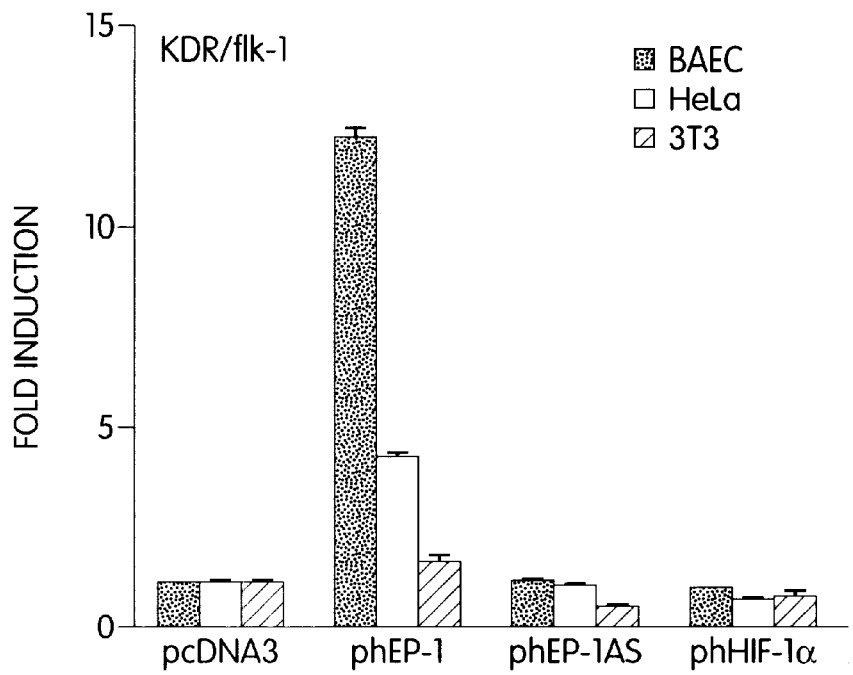
Figure 2B:
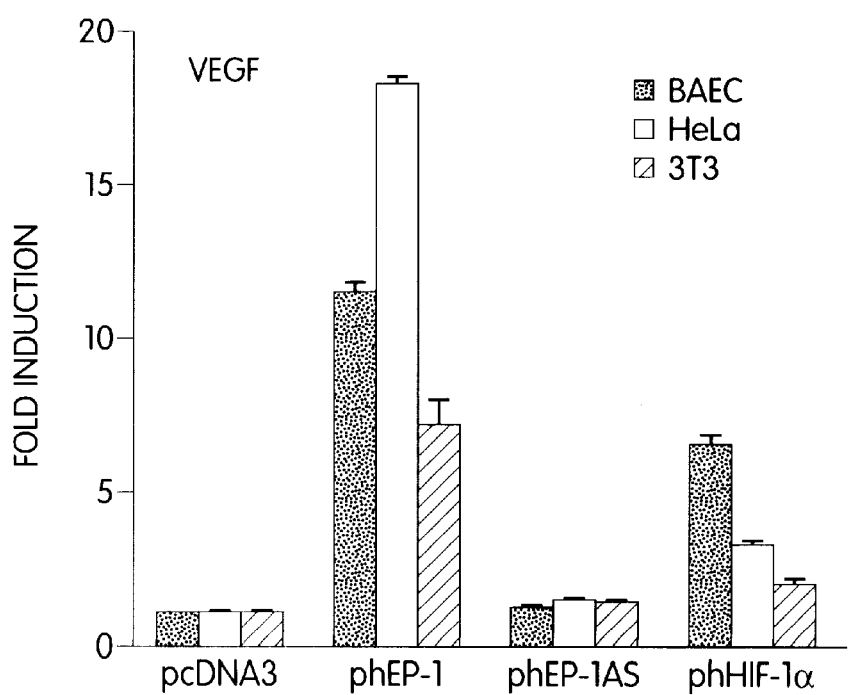
Figure 3B:
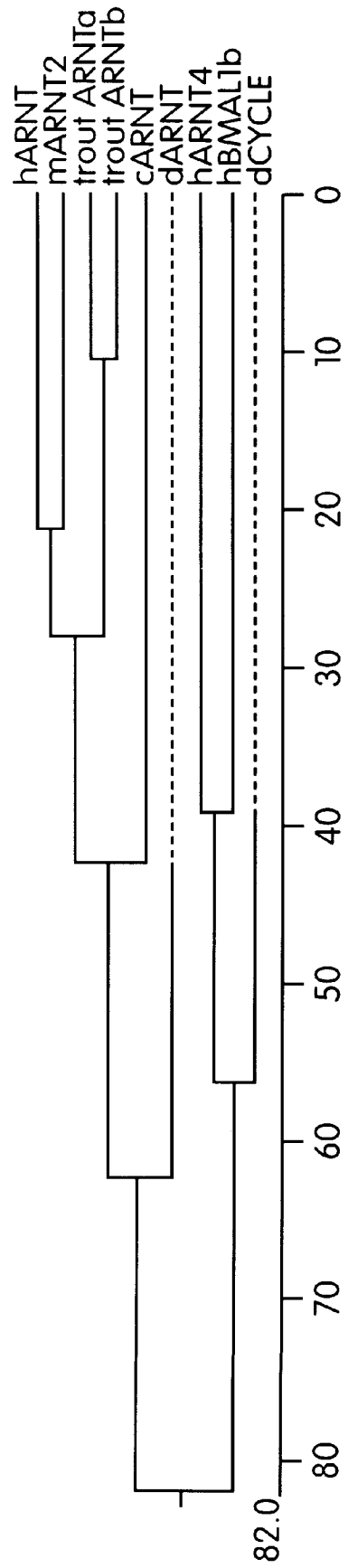
FIG. 3B is a diagram of a phylogenetic tree of the ARNT family of proteins.

EPAS1 but not HIF-1α Transactivates the KDR/flk-1 Promoter Preferentially in Vascular Endothelial Cells To determine whether another member of the bHLH/PAS family transactivated the KDR/flk-1 promoter, the EPAS1 or HIF-1α expression plasmid and the KDR/flk-1 plasmid pGL2-4 kb+296 were cotransfected into BAEC, HeLa cells, and NIH 3T3 cells. EPAS1 expression plasmids in the sense (phEP-1) but not the antisense (phEP-1AS) orientation activated the KDR/flk-1 promoter (FIG. 2A), indicating that the transactivating effect is cell-specific. Although the EPAS1 plasmid markedly increased KDR/flk-1 promoter activity in vascular endothelial cells, it had little effect on KDR/flk-1 promoter activity in HeLa or NIH 3T3 cells (FIG. 2A). HIF-1α had no effect on KDR/flk-1 promoter activity in all three cell types. The EPAS1 or HIF-1α expression plasmid was then cotransfected with a reporter plasmid containing the VEGF promoter, pVR47/CAT, to determine whether the differential effects of EPAS1 and HIF-1α were unique to the KDR/flk-1 promoter. In contrast to its cell-specific effect on the KDR/flk-1 promoter (FIG. 2A), EPAS1 transactivated the VEGF promoter in all three cell types (FIG. 2B). Induction was highest in HeLa cells. Furthermore, HIF-1α increased VEGF promoter activity in BAEC and HeLa cells (FIG. 2B). These data indicate that the transactivating effect of EPAS1 depends on both the promoter and the cell type.

Although EPAS1 transactivated the KDR/flk promoter preferentially in endothelial cells (FIG. 2A), it activated the VEGF promoter in a non-endothelial cell-specific manner (FIG. 2B). Despite the fact that HIF-1α is 48% homologous to EPAS1, HIF-1α had no effect on the KDR/flk-1 promoter. In contrast, HIF-1α transactivated the VEGF promoter. Thus, the effect of EPAS1 on the KDR/flk-1 promoter is specific and cannot be replaced by other members of the PAS family of transcription factors.

EPAS1 heterodimerizes with the aryl hydrocarbon receptor nuclear translocator and transactivates the promoter of Tie2. EPAS1 also markedly increases the promoter activity of KDR/flk-1 and VEGF. Mice deficient in the aryl hydrocarbon receptor nuclear translocator are not viable past E10.5, and the yolk sac shows defective angiogenesis. These data indicate that EPAS1 functions as a nodal transcription factor by regulating expression of VEGF, KDR/flk-1, and Tie2 during vasculogenesis and angiogenesis. Characterization of functional domains of EPAS1

Functional domains of EPAS1 were identified as follows. The gene encoding VEGF has a cis-acting regulatory sequence to which EPAS1 binds (GCCCTACGTGCTGTCTCA; SEQ ID NO: 1) in its 5' flanking region. In cotransfection experiments in BAEC, the EPAS1 expression plasmid activated by 30-fold a CAT reporter plasmid containing 2.3 kb of VEGF 5' flanking sequence (containing SEQ ID NO: 1), but not a similar plasmid differing only by a mutation nucleotide of SEQ ID NO: 1. These data indicate that EPAS1 activates the VEGF promoter by binding to DNA containing the sequence of SEQ ID NO: 1. To further characterize domains of EPAS1 which function to activate promoters of angiogenic factors in endothelial cells, e.g., the VEGF promoter or VEGF-R promoters, BAEC were cotransfected with expression plasmids encoding EPAS1 mutants and the reporter plasmid. Eight mutants were tested. Deletion of the basic region (bHLH region) of EPAS1 (SEQ ID NO:3) completely abolished its ability to induce transcription from the VEGF promoter, indicating that binding of EPAS1 to the cis-acting element though this basic region is critical. Deletion of 180 amino acids from the C-terminus of EPAS1 has little or no effect on the transcriptional transactivation activity of EPAS1 for the VEGF promoter; however, a deletion of the C-terminal 385 amino acids abolished the ability of EPAS1 to activate the VEGF promoter, indicating the presence of transactivation domain in the portion of EPAS1 spanning amino acids 486–690. Further fine deletion analyses indicated that the transactivation domain of EPAS1 spans amino acids 486–639. An EPAS1 mutant polypeptide lacking the amino acid sequence of SEQ ID No:2, e.g., an EPAS1 with the amino acid sequence of SEQ ID No:4, functions as a dominant negative mutant EPAS1 because it inhibited transactivation of the VEGF promoter by wild type EPAS1 in a dose-dependent manner. Deletion analysis is also used to identify domains of EPAS1 which participate in heterodimer formation with ARNT4.

To characterize domains of ARNT4 which function to heterodimerize with EPAS1 and activate promoters of angiogenic factors in endothelial cells, e.g., the VEGF promoter or VEGF-R promoters, BAEC are cotransfected with expression plasmids encoding EPAS1 and ARNT4 deletion mutants and the reporter plasmid as described above. Domains of ARNT4 which participate in EPAS1 heterodimer formation with EPAS1 are identified using the yeast two-hybrid assay or a gel mobility assay. For example, those mutants which fail to activate the VEGF/luciferase promoter cannot form functional dimers with EPAS1.

This assay is also used to identify compounds which inhibit or decrease formation of functional ARNT4/EPAS1 heterodimers, and thus, inhibit angiogenesis. In such an assay, expression plasmids which encode wild type or functional fragments of ARNT4 and EPAS1 are cotransfected with a VEGF/luciferase reporter plasmid into an endothelial cell in the presence and absence of a candidate compound. A decrease in the amount of transactivation of the VEGF promoter (e.g., as measured by a standard luciferase assay) in the presence of the compound compared to the amount in the absence of the candidate compound indicates that the compound inhibits angiogenesis (by inhibiting ARNT4/EPAS1 transactivation of the VEGF promoter).

Generation of a Dominant-Negative EPAS1 Mutants

Figure 5:
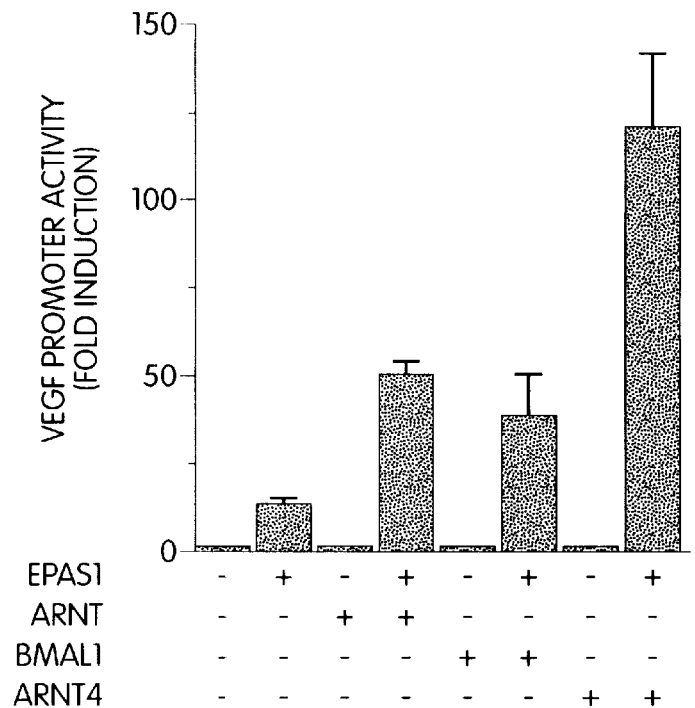
FIG. 5 is a bar graph showing that EPAS1 interacts with ARNT4 to form functional heterodimers which increase VEGF promoter activity and VEGF expression.
Figure 6:
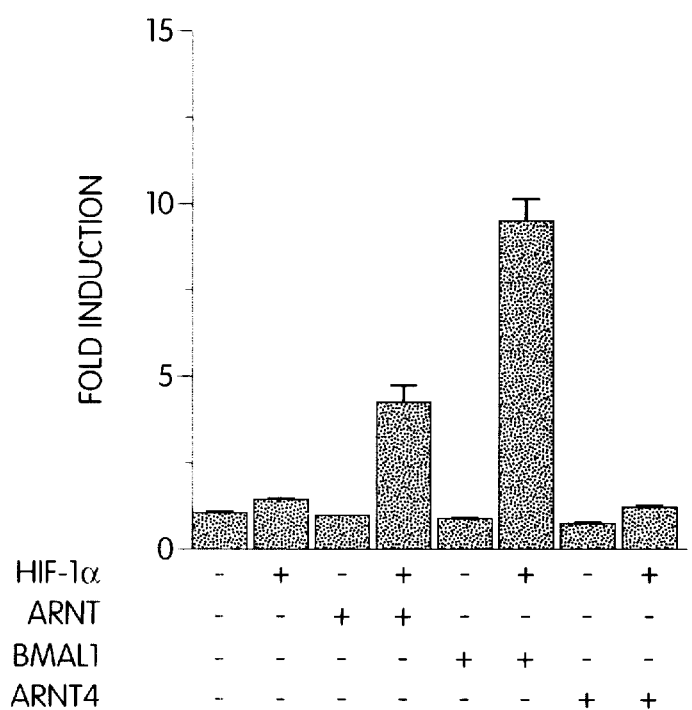
FIG. 6 is a bar graph showing that ARNT4 does not interact with HIF-1α.

An adenoviral construct which expresses EPAS1 was generated. Overexpression of EPAS1 dramatically induced VEGF MRNA in human umbilical endothelial cells. In cotransfection experiments, EPAS1 transactivated the VEGF promoter via the HIF-1 binding site. This transactivation was further enhanced by hypoxia. Cotransfection of an aryl hydrocarbon receptor nuclear translocator (ARNT) expression plasmid and EPAS1 expression plasmid synergistically transactivated the VEGF promoter, indicating that heterodimerization of EPAS1 and ARNT is crucial for the transactivation of the VEGF promoter (FIG. 5). Using a gel shift analysis, EPAS1 (but not HIF-1) formed dimers with ARNT4 and bound to the HIF-1 binding site of the VEGF promoter.

Deletion analysis of EPAS1 further defined a potent transactivation domain to span amino acids 486–639 of human EPAS1 (SEQ ID NO:6). The transactivation domain is essential for EPAS1 to transactivate the VEGF promoter. The ability of this domain to activate transcription was confirmed using the GAL4 fusion protein system. Finally, a truncated EPAS1 lacking the transactivation domain (e.g., an EPAS1 polypeptide lacking amino acids 486–690 of SEQ ID NO:6 or an EPAS1 polypeptide lacking amino acids 486–639 of SEQ ID NO:6) retained its ability to form heterodimers and to bind the HIF-1 binding site. These data indicate that the mutated EPAS1 polypeptides with lack amino acids in the transactivation domain are dominant negative mutants because they sequester ARNT and prevent the formation of functional EPAS1/ARNT and HIF-1α/ARNT heterodimers. For example, the EPAS1 polypeptide which lacked amino acids 486–639 of SEQ ID NO:6 potently inhibited the induction of the VEGF promoter by EPAS1 and HIF-1α. Transfection of endothelial cells with an adenovirus construct encoding this mutant inhibited VEGF mRNA induction by hypoxia. These results indicate that EPAS1 is an important regulator of VEGF gene expression and that dominant negative EPAS1 mutants (e.g., EPAS1 polypeptides lacking all or part of the transactivation domain (SEQ ID NO:2)) inhibit VEGF promoter activity, and in turn, VEGF expression and angiogenesis.

Identification of Compounds Which Modulate EPAS1 Binding to Cis-Regulatory Sequences Modulation of the angiogenesis is achieved by contacting the vascular cells such as vascular endothelial cells with a compound that blocks or enhances EPAS1 binding to cis-acting regulatory sequences of VEGF, VEGF-Rs, or other angiogenic factors in endothelial cells such as Tie2. Such a compound can be identified by methods ranging from rational drug design to screening of random compounds. The latter method is preferable, as simple and rapid assays for testing such compounds are available. Oligonucleotides and small organic molecules are desirable candidate compounds for this analysis.

The screening of compounds for the ability to modulate angiogenesis by affecting EPAS1 transactivation of transcription of angiogenic factors may be carried out using in vitro biochemical assays, cell culture assays, or animal model systems. For example, in a biochemical assay, labeled EPAS1 (e.g., EPAS1 labeled with a fluorochrome or a radioisotope) is applied to a column containing immobilized DNA containing the cis-acting regulatory sequence. Alternatively, ARNT4 is immobilized on the column. In this manner, compounds which inhibit ARNT4/EPAS1 heterodimerization may be identified. A candidate compound is applied to the column before, after, or simultaneously with the labeled EPAS1, and the amount of labeled protein bound to the column in the presence of the compound is determined by conventional methods. A compound tests positive for inhibiting EPAS1 binding (thereby having the effect of inhibiting angiogenesis) if the amount of labeled protein bound in the presence of the compound is lower than the amount bound in its absence. Conversely, a compound tests positive for enhancing EPAS1 binding (thereby having the effect of enhancing angiogenesis) if the amount of labeled protein bound in the presence of the compound is greater than the amount bound in its absence. In a variation of the above-described biochemical assay, binding of labeled DNA to immobilized EPAS1 is measured.

As mentioned above, candidate compounds may also be screened using cell culture assays. Cells expressing EPAS1, either naturally or after introduction into the cells of genes encoding EPAS1 are cultured in the presence of the candidate compound. The level of EPAS1 binding in the cell may be inferred using any of several assays. For example, levels of expression of EPAS1 regulated genes (e.g., genes encoding VEGF, VEGF-Rs such as KDR/flk-1 or flt-1) in the cell may determined using, e.g., Northern blot analysis, RNAse protection analysis, immunohistochemistry, or other standard methods. Compounds identified as having the desired effect, either enhancing or inhibiting EPAS1 binding, can be tested further in appropriate animal models, e.g., an animal with a tumor or atherosclerotic lesion.

Compounds found to inhibit EPAS1 binding to cis-acting regulatory sequences of genes encoding angiogenic factors may be used in methods for inhibiting pathogenic angiogenesis in order to, e.g., prevent or treat tumor progression or the progression of an atherosclerotic lesion. Compounds found to enhance EPAS1 binding may be used in methods to therapeutically promote new blood vessel formation in adult mammals as discussed above.

The therapeutic compounds identified using the methods of the invention may be administered to a patient by any appropriate method for the particular compound, e.g., orally, intravenously, parenterally, transdermally, transmucosally, by inhalation, or by surgery or implantation at or near the site where the effect of the compound is desired (e.g., with the compound being in the form of a solid or semi-solid biologically compatible and resorbable matrix). Therapeutic doses are determined specifically for each compound, most being administered within the range of 0.001 to 100.0 mg/kg body weight, or within a range that is clinically determined to be appropriate by one skilled in the art.

Identification and Molecular Cloning of the EPAS1 Binding Partner ARNT-4

Compositions which interact with EPAS1 were identified by screening for endothelial cell proteins which bind to EPAS1. Yeast two hybrid screening of a human umbilical endothelial cell cDNA library was carried out using EPAS1 as a bait. One of the clones isolated encoded a novel bHLH/PAS protein which was found to have similarity with arylhydrocarbon nuclear translocator 3 (Arnt3), a member of bHLH/PAS protein which heterodimerizes with Clock, a gene product involved in regulation of mammalian circadian rhythm. The isolated clone was named ARNT4. As described above, the CLUSTAL W sequence alignment system was used to compare the sequences of ARNT4 with the most closely related known DNA and/or amino acid sequences. With respect to DNA (comparison of coding sequences; untranslated regions excluded), the sequences of HARNT and hARNT4 were found to be 35% identical; the sequences of hBMAL 1b and hARNT4 were found to be 56% identical; and the sequences of hARNT and hBMAL 1b were found to be 37% identical. Nucleotide sequence comparisons using the CLUSTAL W system were carried out using the following parameters: KTUP=2; gap penalty=5; top diagonals=4; and window size=4. With respect to the proteins, the amino acid sequences of hARNT and hARNT4 were found to be 23% identical; the sequences of hBMAL 1b and hARNT4 were found to be 49% identical; and the sequences of hARNT and hBMAL 1b were found to be 26% identical. Amino acid sequence comparisons using the CLUSTAL W system were carried out using the following parameters: KTUP=1; gap penalty=3; top diagonals=5; and window size=5.

Northern analysis of human tissue revealed that this gene is highly expressed in brain, heart and placenta. In the brain, expression was high in the thalamus and amygdala, an almond-shaped component of the limbic system located in the temporal lobe of the brain.

Figure 4:
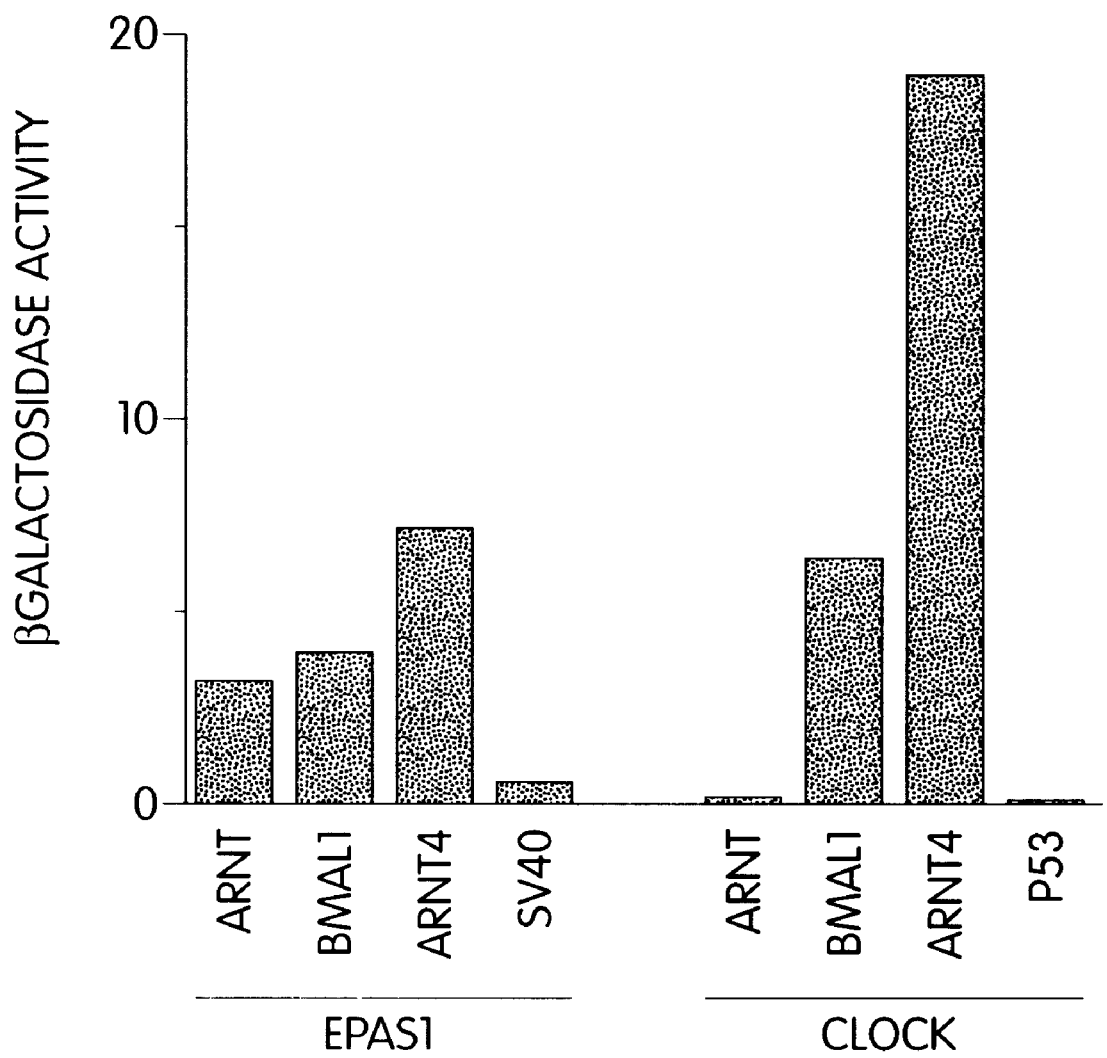
FIG. 4 is a bar graph showing the results of a yeast two-hybrid assay. ARNT3 (BMAL1b) and ARNT4 form heterodimers with EPAS1 as well as with CLOCK.

Expression within human cultured cells demonstrated highest mRNA levels in vascular endothelial cells and smooth muscle cells. ARNT4 was shown to interact with EPAS1 using the yeast two-hybrid assay (FIG. 4). In a gel mobility shift assay using hypoxia responsive element of VEGF gene as the probe, ARNT4 formed a heterodimer with EPAS1 and bound to the hypoxia responsive element of the VEGF gene.

An expression plasmid encoding EPAS1 and an expression plasmid encoding ARNT4 were cotransfected with a VEGF/luciferase reporter plasmid into bovine aortic endothelial cells. Coexpression of ARNT4 and EPAS1 markedly transactivated the VEGF promoter (FIG. 5), and this transactivation was further enhanced by hypoxia. These data indicate that the heterodimer EPAS1/ARNT4 is activated under hypoxic conditions. Taken together, these results indicate that ARNT4, a novel bHLH/PAS protein, is an important regulator of VEGF gene expression especially in vascular system.

TABLE 6

Human ARNT4 amino acid sequence

|     |   |   |   |   |   |   |   |   |   |   |   |   |   |   |   |   |   |   |   |   |     |
|-----|---|---|---|---|---|---|---|---|---|---|---|---|---|---|---|---|---|---|---|---|-----|
|     | M | A | A | E | E |   |   |   |   |   |   |   |   |   |   |   |   |   |   |   | 5 (SEQ ID NO:19) |
| 6   | E | A | A | G | G | K | V | L | R | E | E | N | Q | C | I | A | P | V | V |   | 25  |
| 26  | S | S | R | V | S | P | G | T | R | P | T | A | M | G | S | F | S | S | H | M | 45  |
| 46  | T | E | F | P | R | K | R | K | G | S | D | S | D | P | S | Q | V | E | D | G | 65  |
| 66  | E | H | Q | V | K | M | K | A | F | R | E | A | H | S | Q | T | E | K | R | R | 85  |
| 86  | R | D | K | M | N | N | L | I | E | E | L | S | A | M | I | P | Q | C | N | P | 105 |

TABLE 6-continued

Human ARNT4 amino acid sequence

106 M A R K L D K L T V L R M A V Q H L R S 125

126 L K G L T N S Y V G S N Y R P S F L Q D 145

146 N E L R H L I L K T A E G L F V V G C 165

166 E R G K I L F V S K S V S K I L N Y D Q 185

186 A S L T G Q S L F D F L H P K D V A K V 205

206 K E Q L S S F D I S P R E K L I D A K T 225

226 G L Q V H S N L H A G R T R V Y S G S R 245

246 R S F F C R I K S C K I S V K E E H G C 265

266 L P N S K K K E H R K F Y T I H C T G Y 285

286 L R S W P P N I V G M E E R N S K K D 305

306 N S N F T C L V A I G R L Q P Y I V P Q 325

326 N S G E I N V K P T E F I T R F A V N G 345

346 K F V Y V D Q R A T A I L G Y L P Q E L 365

366 L G T S C Y E Y F H Q D D H N N L T D K 385

386 H K A V L Q S K E K I L T D S Y K F R A 405

406 K D G S F V T L K S Q W F S F T N P W T 425

426 K E L E Y I V S V N T L V L G H S E P G 445

446 E A S F L P C S S Q S S E E S S R Q S C 465

466 M S V P G M S T G T V L G A G S I G T D 485

486 I A N E I L D L Q R L Q S S S Y L D D S 505

506 S P T G L M K D H T V N C R S M S N K 525

526 E L F P P S P S E M G E L E A T R Q N Q 545

546 S T V A V H S H E P L L S D G A Q L D F 565

566 D A L C D N D D T A M A A F M N Y L E A 585

586 E G G L G D P G D F S D I Q W T L 602

TABLE 7

Human ARNT4 cDNA ctccagtccgcatgctcagtagctgctgccggccgggctgcggggcggcgtccgctgcgc (SEQ ID NO:20)

gcctacgggctgcggtggcggccgccgcggcacccggcagggcccgccagtccccgcttc cctgctccagagccgccgcctgggccggggcagggcgggcccggggctcctccatgctgc cagccgccgggctgcggagccgaccaagtggctcctgcg ATG GCG GCG GAA GAG

GAG GCT GCG GCG GGA GGT AAA GTG TTG AGA GAG GAG AAC CAG TGC

ATT GCT CCT GTG GTT TCC AGC CGC GTG AGT CCA GGG ACA AGA CCA

ACA GCT ATG GGG TCT TTC AGC TCA CAC ATG ACA GAG TTT CCA CGA

AAA CGC AAA GGA AGT GAT TCA GAC CCA TCC CAA GTG GAA GAT GGT

GAA CAC CAA GTT AAA ATG AAG GCC TTC AGA GAA GCT CAT AGC CAA

ACT GAA AAG CGG AGG AGA GAT AAA ATG AAT AAC CTG ATT GAA GAA

CTG TCT GCA ATG ATC CCT CAG TGC AAC CCC ATG GCG CGT AAA CTG

TABLE 7-continued

Human ARNT4 cDNA

GAC AAA CTT ACA GTT TTA AGA ATG GCT GTT CAA CAC TTG AGA TCT
TTA AAA GGC TTG ACA AAT TCT TAT GTG GGA AGT AAT TAT AGA CCA
TCA TTT CTT CAG GAT AAT GAG CTC AGA CAT TTA ATC CTT AAG ACT
GCA GAA GGC TTC TTA TTT GTG GTT GGA TGT GAA AGA GGA AAA ATT
CTC TTC GTT TCT AAG TCA GTC TCC AAA ATA CTT AAT TAT GAT CAG
GCT AGT TTG ACT GGA CAA AGC TTA TTT GAC TTC TTA CAT CCA AAA
GAT GTT GCC AAA GTA AAG GAA CAA CTT TCT TCT TTT GAT ATT TCA
CCA AGA GAA AAG CTA ATA GAT GCC AAA ACT GGT TTG CAA GTT CAC
AGT AAT CTC CAC GCT GGA AGG ACA CGT GTG TAT TCT GGC TCA AGA
CGA TCT TTT TTC TGT CGG ATA AAG AGT TGT AAA ATC TCT GTC AAA
GAA GAG CAT GGA TGC TTA CCC AAC TCA AAG AAG AAA GAG CAC AGA
AAA TTC TAT ACT ATC CAT TGC ACT GGT TAC TTG AGA AGC TGG CCT
CCA AAT ATT GTT GGA ATG GAA GAA GAA AGG AAC AGT AAG AAA GAC
AAC AGT AAT TTT ACC TGC CTT GTG GCC ATT GGA AGA TTA CAG CCA
TAT ATT GTT CCA CAG AAC AGT GGA GAG ATT AAT GTG AAA CCA ACT
GAA TTT ATA ACC CGG TTT GCA GTG AAT GGA AAA TTT GTC TAT GTA
GAT CAA AGG GCA ACA GCG ATT TTA GGA TAT CTG CCT CAG GAA CTT
TTG GGA ACT TCT TGT TAT GAA TAT TTT CAT CAA GAT GAC CAC AAT
AAT TTG ACT GAC AAG CAC AAA GCA GTT CTA CAG AGT AAG GAG AAA
ATA CTT ACA GAT TCC TAC AAA TTC AGA GCA AAA GAT GGC TCT TTT
GTA ACT TTA AAA AGC CAA TGG TTT AGT TTC ACA AAT CCT TGG ACA
AAA GAA CTG GAA TAT ATT GTA TCT GTC AAC ACT TTA GTT TTG GGA
CAT AGT GAG CCT GGA GAA GCA TCA TTT TTA CCT TGT AGC TCT CAA
TCA TCA GAA GAA TCC TCT AGA CAG TCC TGT ATG AGT GTA CCT GGA
ATG TCT ACT GGA ACA GTA CTT GGT GCT GGT AGT ATT GGA ACA GAT
ATT GCA AAT GAA ATT CTG GAT TTA CAG AGG TTA CAG TCT TCT TCA
TAC CTT GAT GAT TCG AGT CCA ACA GGT TTA ATG AAA GAT ACT CAT
ACT GTA AAC TGC AGG AGT ATG TCA AAT AAG GAG TTG TTT CCA CCA
AGT CCT TCT GAA ATG GGG GAG CTA GAG GCT ACC AGG CAA AAC CAG
AGT ACT GTT GCT GTC CAC AGC CAT GAG CCA CTC CTC AGT GAT GGT
GCA CAG TTG GAT TTC GAT GCC CTA TGT GAC AAT GAT GAC ACA GCC
ATG GCT GCA TTT ATG AAT TAC TTA GAA GCA GAG GGG GGC CTG GGA
GAC CCT GGG GAC TTC AGT GAC ATC CAG TGG ACC CTC tagcctttgattttt aactccaaaaatgagaaacattttaaagcattatttacgaaaaaa
ctgtctcaactattcttaagtactgtattgatattgtttgtatcttttattaatgttcta
ccactttttatagatttgcatcttcctgtcacagggatgtggggaaatacgttttcctcc
caagagaaccaagtttattatagactcctttattcagtgaaatggcttataatccactag
ttgccatattttt gctaaaatatttctaaccaagaatactacttacatattgttttggct TABLE 7-continued Human ARNT4 cDNA ttgttttattttttgatgcagttttttttagttgaggtaatgtaatatattgatgttttcc tttgtgtctaagattgatttataatagtaggtttgtataatttggaacattttccatgcc ttgcgaatttccttaattgaggatagggcttacacactttaagaaaacagtgagtacttg aacatttaaagggacagtgcaatttatagtcataatcacattgaatactgtatttgatct ttggagacttaggcaagcacagagctgggatatttatgctcagttgagcactttaagatg aattttaagtgagatgatttcttgcttaaaactcagaaagtcaaaagagtttcagctttc cttacagaaaaggaaggatcttgggccctagatcttggggattaacctctgcatataaga tttactcttaataggccagacgtggtgctcacgcctgtaatcccagtactttgggaggct gagacgggcagatcacttgaggtcaggagttcaagaccagcctggccaatatggtgaaac cccgtttctactaaaaatacaaaaaaaattacccaggcactcactcttgaggtaactaac caactcccacgataatgacagtccattcatgagcgcaaaggcctcatgacctaatggcac acacctgtaatcccaactgcttgggaggctgaggcgagaggattgcttgaacctgggagg cagaggttgcagtgagccgagatcgcaccactgcactccagtctgggcaacagagtgaga cttcatctcaaaaaaagtaaaaaaaaagatttaatataatcactgaagatctctattata gatagattaggtttttgacattggaaacatacttagggatagatttgtcctaaaggaaaa aagtaggcccgggcagattaaatgtcttgtgtaaagtcacacattaaattcagtcacaca ttaaattcatagagttttaaatgtttaatgtatataaaccagtttctttatacacatttg ggaaaacattggtctcacagattaaatgattaactaactgacccaggaactagttgtagc tttctaagtaattaggcaattacagttattgcctgtaaccaaaggtaataaaacaaaatg acaagtacatgtttaaaattatgaggcaatgagaaataatttaaaaaccaattttctagt tataatttaaaatttggagagcattttaacagtaattaatccagaggtggctcaaattg agtataagaattaagattatttaaaatactgcatgtctaccttctcgggatcatacttt ataacactttctgcttcahtagctcttcatagcttgccaagtatgctcccatattttctc tctcgtgcctcgcaaatgaaagtcagataggctgggaactcatggggcagccctcagact tcaatgtgggcttcaaatccagtttcctgttctatatggtgctacatctttccagaaaat ttccctcagagcccctcgccaaaacaaagcattattttgaccctgcatgctatttcttta gctgtaggtgatagattagaacttctgtcagacatgttaatgacaaacataccaacagac aataaccaaagcaaatgtttccttcaagtgtgaaatgtgcaggggctcgtgggcaaggat gtattggcacactgtcctcttgaactgatagtgtcccagcaatgttggaggttggcacca ttcctggtccgacacttgaggacctgagagacatcaggtttagaatgagccaaagaaatc ctacaagatggggagaattggtgtgcagcagcctaagtgttatagttaagtctaaagaag tatgaaagatcccctgtgttctctaaattgagcagaggggcctgcctaccaatatcactt tttaggggactgaaccattgcaggttagacttggcttccaaagagtctgcctaagccagg ggtggcagggtaggccatcatagctggatggcctcaaaagcagatgggggcagacttgcc ctcgtgatgccaggatttgagaggcagagtttctagagggagaccagtgctgcctctcac agtggcagttttttctctttgcaagaggaggggctgttcaattccatagaccagtgggca gatagccagttgaatactctgtgcatggtttgatcctttattagttcgctctaatatttt tctgtagatccttttgtcctggactcaaaatctaatccatgcattgtatgataccgtagc tctcctaaggtttgtgtttccttcaaaatgttttagttttcttcaactaaatttgatttt

TABLE 7-continued

Human ARNT4 cDNA tgctgttagaagtgacatattttatggtatacactatgttcctttttctactgcgagt caattttttgaattttcgtgagaaagaatatatctacaaattgcacgaaagtatcataaa aacagtactctagagcagcgctgtccaatagaaatataatctgagccacatgtataattt tattttcttctagccacattaaagaagtaaaaagatacaagtagaactaattttaatgtt ttaattcagtatatccaaaatatcatttgaacatgtaattaatataaaattattaatgtg atattttacattcttttggtaatactagtcttcaaaatctggtatgtatcttacattgat agcacatctcactttgtactagccacattgcaagtgctcagtagccacatgtggctagtg gctactgcactggacagcacagttctaggttccaccctaacacccaagtcctgtggatta gaatcccagaatcagagctggaagtaaacatagagatcaaacctcctttaaaaatgagg acgctgaggcacagagtttaaatggcttgcatgaggtcatacagctaaattcagcctcaa cagggtcttctgattccaggcactcttcccactccactacattactgtagtggtaattct tagggttaaaaaaagtgtagagtaggccgggcgcagtggctcatgcctgtaatcccagca ctttgggaggccgaagtgggcggatcacgaggtcaggagatcgagaccatcctggccaac atggtgaaacccgtctctactgaaaatacaaagcaaaattagccaggtgtggtggcggg cgcctgtggtcccagctgctctggaggctgaggcagaatggcgtgaacccaggaggcaga gatggcagtgagccaagatcgcgccactgcacccagcctgggcgacagagcgagactcc atctcaaaaaaaaaaaaaaaaaaaagaaaagaaaagaaaagtctagagaacattatat taagtggttattattgaagtagaccaaagtttataccataaggatattttccttaaata ccatgtttgaagaacaattatttattgatccttgaatctgtaagatcaaataacaagtct ctatccatgttacaaaatttaaccttttgaaaataataaactttaaaatatcagatgtgt tattacaggatgatacttggaatcaagtgaaatgagttatatggtcatcactaaatttag aaatctattgtgaaacaaagacaaacaggaaagtacagaatagagacttttagtaaataa atggaatttaaaagaaagtgtttatttacagtgtcacgacagaaaaggatgtctttgttg tcatagtctttgagggatctccgtaaaatctggggcacaggtacaagaaatagccaatat ttagttcccagaccatgtttagtagtgtccagtttcagatcatgctgccaagaggtatct cccctcaggtgggtcatcactgagccctggaattggagactcatacttgcccagcacaa tgttacgggcagacaggccgacatctatgattagctagaagccataaagaaaagctgcta agtggccactaggtgccacttttctgtttttgtaatgctttcattagcagatctttttt tccaagctccatggggcctatgagaggcatttatgattttgtgcctacaataagtcagc ctgtctggtgtgagttgttttatgagaaatgctttccaagggaggtctaggaagatcctg acacataagaactttggcttagagagctttccaggtgtagtgccaataaaaactgacctg gaaagaaaacctgcccagcacggaacatgctttctgaactcacttgagagtgtatggtgt atgtcacttctcatatattcttgagtttagatttgtcttttatacaattttagctcttt tccagttcacttgtgctcgtctgtatattggtattttaaatttttgtggtaaataatga aaagagtgaaattatattttataattactcatttgtagttttttttttaatttaataaa cttcctccaaaaagtgctcccttaaaa ARNT4 coding sequence in Table 7 is indicated by upper case letters (nucleotides 220 to 2025) with the termination codon underlined.

Diagnosis and Treatment of Circadian Rhythm Disorders

ARNT4 is involved in regulating circadian rhythm, e.g., by forming a heterodimer with Clock, a protein that regulates the timing of fatigue and alertness. Individuals with circadian rhythm disorders are screened for mutations in the an ARNT4 gene product or ARNT4 gene, e.g,. by detecting restriction fragment length polymorphisms (RFLPs) or by PCR. Individuals with symptoms of circadian rhythm disorders and identified as having a mutated ARNT4 gene are treated by administering DNA encoding a normal ARNT4 gene product. For example, DNA containing the coding sequence of SEQ ID NO:20 is administered to such individuals using standard gene therapy techniques described herein. Similarly, an abnormally low or high level of ARNT4 protein or transcript is detected in an individual suffering from such disorders, the levels can be normalized by antisense therapy to inhibit ARNT4 production or gene therapy to augment production. ARNT4 levels may also be altered to artificially regulate circadian rhythm, e.g., to induce long periods of sleep in patients to improve the healing process or in individuals travelling long distances such astronauts during space travel.

Antisense Therapy

Nucleic acids complementary to all or part of the human EPAS1 cDNA (GenBank Accession # U81984; SEQ ID NO:7) may be used in methods for antisense treatment to inhibit expression of EPAS1. Nucleic acids complementary to all or part of the human ARNT4 CDNA (SEQ ID NO:20) may be used in methods for antisense treatment to inhibit expression of ARNT4. Antisense treatment may be carried out by administering to a mammal, such as a human, DNA containing a promoter, e.g., an endothelial cell-specific promoter, operably linked to a DNA sequence (an antisense template), which is transcribed into an antisense RNA. Alternatively, as mentioned above, antisense oligonucleotides may be introduced directly into vascular cells. The antisense oligonucleotide may be a short nucleotide sequence (generally at least 10, preferably at least 14, more preferably at least 20 (e.g., at least 30), and up to 100 or more nucleotides) formulated to be complementary to a portion, e.g., the coding sequence, or all of EPAS1 MRNA or ARNT4 mRNA. For example, the sequence is complementary some or all of the C-terminal activation domain; alternatively, the sequence may be complementary to all or. part of the N-terminal DNA binding domain. The antisense sequence is complementary to DNA encoding residues 75 to 128, inclusive, of SEQ ID NO:19; the antisense sequence. Alternatively, the antisense sequence is complementary to DNA encoding residues 155 to 207, inclusive, of SEQ ID NO:19, or encoding residues 232 to 384 of SEQ ID NO:19., Standard methods of administering antisense therapy have been described (see, e.g., Melani et al., 1991, Cancer Res. 51:2897–2901). Following transcription of a DNA sequence into an antisense RNA, the antisense RNA binds to its target nucleic acid molecule, such as an mRNA molecule, thereby inhibiting expression of the target nucleic acid molecule. For example, an antisense sequence complementary to a portion or all of EPAS1 mRNA could be used to inhibit the expression of EPAS1, thereby decreasing the level of transcription of angiogenic factors such as VEGF or VEGF-Rs, which in turn leads to a decrease in new blood vessel formation. Oligonucleotides complementary to various portions of EPAS1 mRNA or ARNT4 MRNA can readily be tested in in vitro for their ability to decrease production of their respective gene products, using assays similar to those described herein. Sequences which decrease production of EPAS1 message or ARNT4 message in vitro cell-based or cell-free assays can then be tested in vivo in rats or mice to determine whether blood vessel formation is decreased.

Preferred vectors for antisense templates are viral vectors, including those derived from replication-defective hepatitis viruses (e.g., HBV and HCV), retroviruses (see, e.g., WO 89/07136; Rosenberg et al., 1990, N. Eng. J. Med. 323(9) :570–578), adenovirus (see, e.g., Morsey et al., 1993, J. Cell. Biochem., Supp. 17E,), adeno-associated virus (Kotin et al., 1990, Proc. Natl. Acad. Sci. USA 87:2211–2215,), replication defective herpes simplex viruses (HSV; Lu et al., 1992, Abstract, page 66, Abstracts of the Meeting on Gene Therapy, September 22–26, Cold Spring Harbor Laboratory, Cold Spring Harbor, N.Y.), and any modified versions of these vectors. The invention may utilize any other delivery system which accomplishes in vivo transfer of nucleic acids into eucaryotic cells. For example, the nucleic acids may be packaged into liposomes, receptor-mediated delivery systems, non-viral nucleic acid-based vectors, erythrocyte ghosts, or microspheres (e.g., microparticles; see, e.g., U.S. Pat. No. 4,789,734; U.S. Pat. No. 4,925,673; U.S. Pat. No. 3,625,214; Gregoriadis, 1979, Drug Carriers in Biology and Medicine, pp. 287–341 (Academic Press,). Alternatively, naked DNA may be administered. Delivery of nucleic acids to a specific site in the body for antisense therapy may also be accomplished using a biolistic delivery system, such as that described by Williams et al., 1991, Proc. Natl. Acad. Sci. USA 88:2726–2729.

Antisense oligonucleotides may consist of DNA, RNA, or any modifications or combinations thereof. As an example of the modifications that the oligonucleotides may contain, inter-nucleotide linkages other than phosphodiester bonds, such as phosphorothioate, methylphosphonate, methylphosphodiester, phosphorodithioate, phosphoramidate, phosphotriester, or phosphate ester linkages (Uhlman et al., 1990, Chem. Rev. 90(4): 544–584; Anticancer Research, 1990, 10:1169) may be present in the oligonucleotides, resulting in their increased stability. Oligonucleotide stability may also be increased by incorporating 3'-deoxythymidine or 2'-substituted nucleotides (substituted with, e.g., alkyl groups) into the oligonucleotides during synthesis, by providing the oligonucleotides as phenylisourea derivatives, or by having other molecules, such as aminoacridine or poly-lysine, linked to the 3' ends of the oligonucleotides e.g., Anticancer Research, 1990, 10:1169–1182). Modifications of the RNA and/or DNA nucleotides may be present throughout the oligonucleotide, or in selected regions of the oligonucleotide, e.g., in the 5' and/or 3' ends. The antisense oligonucleotides may also be modified so as to increase their ability to penetrate the target tissue by, e.g., coupling the oligonucleotides to lipophilic compounds. Antisense oligonucleotides based on the human EPAS1 nucleotide sequence (SEQ ID NO:7) or the human ARNT4 nucleotide sequence (SEQ ID NO:20) can be made by any method known in the art, including standard chemical synthesis, ligation of constituent oligonucleotides, and transcription of DNA complementary to the all or part of the EPAS1 cDNA or ARNT4 cDNA.

EPAS1 is naturally expressed in vascular endothelial cells. These cells are, therefore, the preferred cellular targets for antisense therapy. Targeting of antisense oligonucleotides to endothelial cells is not critical to the invention, but may be desirable in some instances, e.g. systemic administration of antisense compositions. Targeting may be achieved, for example, by coupling the oligonucleotides to ligands of endothelial cell surface receptors. Similarly, oligonucleotides may be targeted to endothelial cells by being conjugated to monoclonal antibodies that specifically bind to endothelial-specific cell surface proteins. Antisense compositions may also be administered locally, e.g., at the site of an atherosclerotic lesion or at the site of a tumor.

Therapeutic applications of antisense oligonucleotides in general are described, e.g., in the following review articles: Le Doan et al., Bull. Cancer 76:849–852, 1989; Dolnick, Biochem. Pharmacol. 40:671–675, 1990; Crooke, Annu. Rev. Pharmacol. Toxicol. 32, 329–376, 1992. Antisense nucleic acids may be used alone or combined with one or more materials, including other antisense oligonucleotides or recombinant vectors, materials that increase the biological stability of the oligonucleotides or the recombinant vectors, or materials that increase the ability of the therapeutic compositions to penetrate endothelial cells selectively.

Therapeutic compositions, e.g., inhibitors of EPAS1 and/or ARNT4 transcription or transactivating function, may be administered in pharmaceutically acceptable carriers (e.g., physiological saline), which are selected on the basis of the mode and route of administration and standard pharmaceutical practice. Suitable pharmaceutical carriers, as well as pharmaceutical necessities for use in pharmaceutical formulations, are described in Remington's Pharmaceutical Sciences, a standard reference text in this field, and in the USP/NF. The compound may be administered with intravenous fluids as well as in combination with other anti-inflammatory agents, e.g., antibiotics; glucocorticoids, such as dexamethasone (Dex), or other chemotherapeutic drugs for the treatment of atherosclerotic lesions and tumors, respectively.

A therapeutically effective amount is an amount which is capable of producing a medically desirable result in a treated animal. As is well known in the medical arts, dosage for any one patient depends upon many factors, including the patient's size, body surface area, age, the particular compound to be administered, sex, time and route of administration, general health, and other drugs being administered concurrently. Dosages will vary, but a preferred dosage for intravenous administration of DNA is approximately $10^6$ to $10^{22}$ copies of the DNA molecule. The compositions of the invention may be administered locally or systemically. Administration will generally be parenterally, e.g., intravenously. As mentioned above, DNA may also be administered directly to the target site, e.g., by biolistic delivery to an internal or external target site or by catheter to a site in an artery.

Gene Therapy

Compositions which enhance intracellular production of EPAS1 (or its binding to a cis-acting regulatory region of a gene encoding VEGF or a VEGF-R) or ARNT4 may be used in methods to promote new blood vessel formation, e.g., to promote angiogenesis in wound healing (e.g., healing of broken bones, burns, diabetic ulcers, or traumatic or surgical wounds) and organ transplantation. Such compounds may be used to treat peripheral vascular disease, cerebral vascular disease, hypoxic tissue damage (e.g., hypoxic damage to heart tissue), or coronary vascular disease as well as to treat patients who have, or have had, transient ischemic attacks, vascular graft surgery, balloon angioplasty, frostbite, gangrene, or poor circulation.

Since EPAS1 and ARNT4 are nuclear proteins, a preferred method of increasing the levels of these proteins or polypeptides in a cell (to increase transcription of such angiogenic factors as VEGF or VEGF-Rs) is intracellular expression of recombinant EPAS1 or ARNT4 or active fragments thereof, e.g., transactivating fragments. DNA encoding EPAS1 or ARNT4 is administered alone or as part of an expression vector as described above. The DNA introduced into its target cells, e.g., endothelial cells at an anatomical site in need of angiogenesis, directs the production of recombinant EPAS1 or ARNT4 or fragments thereof in the target cell, to enhance production of new blood vessels. For inhibition of angiogenesis, gene therapy are also used to introduce administer DNA encoding a dominant negative mutant of EPAS1 such as DNA encoding a polypeptide with the amino acid sequence of SEQ ID NO:4 or a polypeptide with the amino acid sequence of residues 486–639 of SEQ ID NO:6.

Antibodies and Intrabodies

Anti-EPAS1 antibodies were obtained using techniques well known in the art. Such antibodies can be polyclonal or monoclonal. Polyclonal antibodies can be obtained, for example, by the methods described in Ghose et al., Methods in Enzymology, Vol. 93, 326–327, 1983. An EPAS1 polypeptide, or an antigenic fragment thereof, was used as the immunogen to stimulate the production of EPAS1-reactive polyclonal antibodies in the antisera of animals such as rabbits, goats, sheep, rodents and the like. EPAS1-specific antibodies were raised by immunizing animals with a C-terminal EPAS1 polypeptide spanning amino acids 668–829 of human EPAS (PGGSTSHLMWKRMKNLRGGSCPLMPDKPLSANVPN DKFTQNPMRGL HPLRHLPLPQPPSAISPGENSKSRFP-PQCYATQYQDYSLSSAHKVSGMASRLLGP; (SEQ ID NO:17) and a C-terminal EPAS polypeptide spanning amino acids 641–875 of mouse EPAS1 DPPLHFGPTKWPVGDQ-SAE SLGALPVGSWQLELPSAPLHVSMFKMR-SAKDFGARGPYMMSPAMIALSNK LKLKRQLEY-EEQAFQDTSGGDPPGTSSSHLMWKRMKSLMGGTCP LMPDKT ISANMAPDEFTQKSMRGLGQPLRHLPP-PQPPSTRSSGENAKTGFPPQCYA SQFQDYGPP-GAQKVSGVASRLLGPSFEPYLLPELTRY-DCEVNVPVPGSST LLQGRDLLRALDQAT (SEQ ID NO:18).

Monoclonal antibodies are obtained by the process described by Milstein and Kohler in Nature, 256:495–97, 1975, or as modified by Gerhard, Monoclonal Antibodies, Plenum Press, 1980, pages 370–371. Hybridomas are screened to identify those producing antibodies that are highly specific for an EPAS1 polypeptide. Preferably, the antibody will have an affinity of at least about $10^8$ liters/mole and more preferably, an affinity of at least about $10^9$ liters/mole. Monoclonal antibodies can be humanized by methods known in the art, e.g, MAbs with a desired binding specificity can be commercially humanized (Scotgene, Scotland; Oxford Molecular, Palo Alto, Calif.).

Following identification of a hybridoma producing a suitable monoclonal antibody, DNA encoding the antibody is cloned. DNA encoding a single chain EPAS1-specific antibody in which heavy and light chain variable domains (separated by a flexible linker peptide such as $Gly_4$-$Ser_3$ (SEQ ID NO:16) is cloned into an expression vector using known methods (e.g., Marasco et al., 1993, Proc. Natl. Acad. Sci. USA 90:7889–7893 and Marasco et al., 1997, Gene Therapy 4:11–15). Such constructs are introduced into cells, e.g., using gene therapy techniques described herein, for intracellular production of the antibodies. Intracellular antibodies, i.e., intrabodies, are used to inhibit binding of endogenous EPAS1 to its target DNA (e.g., cis-acting regulatory sequences of genes encoding VEGF or VEGF-Rs), which in turn, decreases production of these angiogenic factors and decreases new blood vessel formation in the treated mammal. Intrabodies which bind to a C-terminal transactivation domain of EPAS1 inhibit the ability of EPAS1 to induce transcription of a gene encoding an angiogenic factor such as VEGF or a VEGF-R. A similar strategy is used to make intrabodies which bind to intracellular ARNT4. Such intrabodies bind to ARNT4 and prevent heterodimeriation with EPAS1, and as a result, inhibit transactivation of the VEGF promoter. Inhibition of VEGF promoter activity, in turn, leads to inhibition of new blood vessel formation.

SEQUENCE LISTING

<160> NUMBER OF SEQ ID NOS: 22

<210> SEQ ID NO 1
<211> LENGTH: 18
<212> TYPE: DNA
<213> ORGANISM: Homo sapiens

<400> SEQUENCE: 1
gccctacgtg ctgtctca                                                                                        18

<210> SEQ ID NO 2
<211> LENGTH: 205
<212> TYPE: PRT
<213> ORGANISM: Homo sapiens

<400> SEQUENCE: 2

```
Glu Asp Tyr Tyr Thr Ser Leu Asp Asn Asp Leu Lys Ile Glu Val Ile
  1               5                  10                  15

Glu Lys Leu Phe Ala Met Asp Thr Glu Ala Lys Asp Gln Cys Ser Thr
             20                  25                  30

Gln Thr Asp Phe Asn Glu Leu Asp Leu Glu Thr Leu Ala Pro Tyr Ile
         35                  40                  45

Pro Met Asp Gly Glu Asp Phe Gln Leu Ser Pro Ile Cys Pro Glu Glu
     50                  55                  60

Arg Leu Leu Ala Glu Asn Pro Gln Ser Thr Pro Gln His Cys Phe Ser
 65                  70                  75                  80

Ala Met Thr Asn Ile Phe Gln Pro Leu Ala Pro Val Ala Pro His Ser
                 85                  90                  95

Pro Phe Leu Leu Asp Lys Phe Gln Gln Gln Leu Glu Ser Lys Lys Thr
            100                 105                 110

Glu Pro Glu His Arg Pro Met Ser Ser Ile Phe Phe Asp Ala Gly Ser
        115                 120                 125

Lys Ala Ser Leu Pro Pro Cys Cys Gly Gln Ala Ser Thr Pro Leu Ser
    130                 135                 140

Ser Met Gly Gly Arg Ser Asn Thr Gln Trp Pro Pro Asp Pro Pro Leu
145                 150                 155                 160

His Phe Gly Pro Thr Lys Trp Ala Val Gly Asp Gln Arg Thr Glu Phe
                165                 170                 175

Leu Gly Ala Ala Pro Leu Gly Pro Pro Val Ser Pro Pro His Val Ser
            180                 185                 190

Thr Phe Lys Thr Arg Ser Ala Lys Gly Phe Gly Ala Arg
        195                 200                 205
```

<210> SEQ ID NO 3
<211> LENGTH: 54
<212> TYPE: PRT
<213> ORGANISM: Homo sapiens

<400> SEQUENCE: 3

Arg Arg Lys Glu Lys Ser Arg Asp Ala Ala Arg Cys Arg Arg Ser Lys

```
                1               5                    10                   15

Glu Thr Glu Val Phe Tyr Glu Leu Ala His G lu Leu Pro Leu Pro His
                                20                  25                  30

Ser Val Ser Ser His Leu Asp Lys Ala Ser I le Met Arg Leu Glu Ile
                    35                  40                  45

Ser Phe Leu Arg Thr His
                50

<210> SEQ ID NO 4
            <211> LENGTH: 485
            <212> TYPE: PRT
            <213> ORGANISM: Homo sapiens

<400> SEQUENCE: 4

Met Thr Ala Asp Lys Glu Lys Lys Arg Ser S er Ser Glu Arg Arg Lys
              1               5                  10                  15

Glu Lys Ser Arg Asp Ala Ala Arg Cys Arg A rg Ser Lys Glu Thr Glu
                            20                  25                  30

Val Phe Tyr Glu Leu Ala His Glu Leu Pro L eu Pro His Ser Val Ser
                        35                  40                  45

Ser His Leu Asp Lys Ala Ser Ile Met Arg L eu Glu Ile Ser Phe Leu
                    50                  55                  60

Arg Thr His Lys Leu Leu Ser Ser Val Cys S er Glu Asn Glu Ser Glu
             65                  70                  75                  80

Ala Glu Ala Asp Gln Gln Met Asp Asn Leu T yr Leu Lys Ala Leu Glu
                            85                  90                  95

Gly Phe Ile Ala Val Val Thr Gln Asp Gly A sp Met Ile Phe Leu Ser
                        100                 105                 110

Glu Asn Ile Ser Lys Phe Met Gly Leu Thr G ln Val Glu Leu Thr Gly
                    115                 120                 125

His Ser Ile Phe Asp Phe Thr His Pro Cys A sp His Glu Glu Ile Arg
                130                 135                 140

Glu Asn Leu Ser Leu Lys Asn Gly Ser Gly P he Gly Lys Lys Ser Lys
            145                 150                 155                 160

Asp Met Ser Thr Glu Arg Asp Phe Phe Met A rg Met Lys Cys Thr Val
                            165                 170                 175

Thr Asn Arg Gly Arg Thr Val Asn Leu Lys S er Ala Thr Trp Lys Val
                        180                 185                 190

Leu His Cys Thr Gly Gln Val Lys Val Tyr A sn Asn Cys Pro Pro His
                    195                 200                 205

Asn Ser Leu Cys Gly Tyr Lys Glu Pro Leu L eu Ser Cys Leu Ile Ile
                210                 215                 220

Met Cys Glu Pro Ile Gln His Pro Ser His M et Asp Ile Pro Leu Asp
            225                 230                 235                 240

Ser Lys Thr Phe Leu Ser Arg His Ser Met A sp Met Lys Phe Thr Tyr
                            245                 250                 255

Cys Asp Asp Arg Ile Thr Glu Leu Ile Gly T yr His Pro Glu Glu Leu
                        260                 265                 270

Leu Gly Arg Ser Ala Tyr Glu Phe Tyr His A la Leu Asp Ser Glu Asn
                    275                 280                 285

Met Thr Lys Ser His Gln Asn Leu Cys Thr L ys Gly Gln Val Val Ser
                290                 295                 300

Gly Gln Tyr Arg Met Leu Ala Lys His Gly G ly Tyr Val Trp Leu Glu
            305                 310                 315                 320
```

```
Thr Gln Gly Thr Val Ile Tyr Asn Pro Arg Asn Leu Gln Pro Gln Cys
                325                 330                 335

Ile Met Cys Val Asn Tyr Val Leu Ser Glu Ile Glu Lys Asn Asp Val
            340                 345                 350

Val Phe Ser Met Asp Gln Thr Glu Ser Leu Phe Lys Pro His Leu Met
        355                 360                 365

Ala Met Asn Ser Ile Phe Asp Ser Ser Gly Lys Gly Ala Val Ser Glu
    370                 375                 380

Lys Ser Asn Phe Leu Phe Thr Lys Leu Lys Glu Glu Pro Glu Glu Leu
385                 390                 395                 400

Ala Gln Leu Ala Pro Thr Pro Gly Asp Ala Ile Ile Ser Leu Asp Phe
                405                 410                 415

Gly Asn Gln Asn Phe Glu Glu Ser Ser Ala Tyr Gly Lys Ala Ile Leu
            420                 425                 430

Pro Pro Ser Gln Pro Trp Ala Thr Glu Leu Arg Ser His Ser Thr Gln
        435                 440                 445

Ser Glu Ala Gly Ser Leu Pro Ala Phe Thr Val Pro Gln Ala Ala Ala
    450                 455                 460

Pro Gly Ser Thr Thr Pro Ser Ala Thr Ser Ser Ser Ser Ser Cys Ser
465                 470                 475                 480

Thr Pro Asn Ser Pro
                485

<210> SEQ ID NO 5
<211> LENGTH: 1607
<212> TYPE: DNA
<213> ORGANISM: Homo sapiens

<400> SEQUENCE: 5
cctgactgcg cggggcgctc gggacctgcg cgcacctcgg accttcacca cccgcccggg      60
ccgcggggag cggacgaggg ccacagcccc ccacccgcca gggagcccag gtgctcggcg     120
tctgaacgtc tcaaagggcc acagcgacaa tgacagctga aaggagaaga aaaggagta     180
gctcggagag gaggaaggag aagtcccggg atgctgcgcg gtgccggcgg agcaaggaga     240
cggaggtgtt ctatgagctg gcccatgagc tgcctctgcc ccacagtgtg agctcccatc     300
tggacaaggc ctccatcatg cgactggaaa tcagcttcct gcgaacacac agctcctct      360
cctcagtttg ctctgaaaac gagtccgaag ccgaagctga ccagcagatg gacaacttgt     420
acctgaaagc cttggagggt ttcattgccg tggtgaccca agatggcgac atgatctttc     480
tgtcagaaaa catcagcaag ttcatggac ttacacaggt ggagctaaca ggacatagta     540
tctttgactt cactcatccc tgcgaccatg aggagattcg tgagaacctg agtctcaaaa     600
atggctctgg ttttgggaaa aaagcaaag acatgtccac agagcgggac ttcttcatga     660
ggatgaagtc cacggtcacc aacagaggcc gtactgtcaa cctcaagtca gccactgga      720
aggtcttgca ctgcacgggc aggtgaaag tctacaacaa ctgccctcct cacaatagtc     780
tgtgtggcta caaggagccc ctgctgtcct gcctcatcat catgtgtgaa caatccagc      840
acccatccca catggacatc cccctggata gcaagacctt cctgagccgc acagcatgg      900
acatgaagtt cacctactgt gatgacagaa tcacagaact gattggttac ccctgagg      960
agctgcttgg ccgctcagcc tatgaattct accatgcgct agactccgag acatgacca     1020
agagtcacca gaacttgtgc accaagggtc aggtagtaag tggccagtac cggatgctcg    1080
caaagcatgg gggctacgtg tggctggaga cccaggggac ggtcatctac acccctcgca    1140
```

```
acctgcagcc ccagtgcatc atgtgtgtca actacgtcct gagtgagatt g agaagaatg    1200 acgtggtgtt ctccatggac cagactgaat ccctgttcaa gccccacctg a tggccatga    1260 acagcatctt tgatagcagt ggcaaggggg ctgtgtctga aagagtaac t tcctattca    1320 ccaagctaaa ggaggagccc gaggagctgg cccagctggc tccaccccca g gagacgcca    1380 tcatctctct ggatttcggg aatcagaact tcgaggagtc ctcagcctat g gcaaggcca    1440 tcctgccccc gagccagcca tgggccacgg agttgaggag ccacagcacc c agagcgagg    1500 ctgggagcct gcctgccttc accgtgcccc aggcagctgc cccgggcagc a ccaccccca    1560 gtgccaccag cagcagcagc agctgctcca cgcccaatag cccttga                   1607

<210> SEQ ID NO 6
<211> LENGTH: 870
<212> TYPE: PRT
<213> ORGANISM: Homo sapiens

<400> SEQUENCE: 6
```

Met Thr Ala Asp Lys Glu Lys Lys Arg Ser S er Ser Glu Arg Arg Lys
1               5                   10                  15

Glu Lys Ser Arg Asp Ala Ala Arg Cys Arg A rg Ser Lys Glu Thr Glu
            20                  25                  30

Val Phe Tyr Glu Leu Ala His Glu Leu Pro L eu Pro His Ser Val Ser
        35                  40                  45

Ser His Leu Asp Lys Ala Ser Ile Met Arg L eu Glu Ile Ser Phe Leu
    50                  55                  60

Arg Thr His Lys Leu Leu Ser Ser Val Cys S er Glu Asn Glu Ser Glu
65                  70                  75                  80

Ala Glu Ala Asp Gln Gln Met Asp Asn Leu T yr Leu Lys Ala Leu Glu
                85                  90                  95

Gly Phe Ile Ala Val Thr Gln Asp Gly A sp Met Ile Phe Leu Ser
            100                 105                 110

Glu Asn Ile Ser Lys Phe Met Gly Leu Thr G ln Val Glu Leu Thr Gly
        115                 120                 125

His Ser Ile Phe Asp Phe Thr His Pro Cys A sp His Glu Glu Ile Arg
    130                 135                 140

Glu Asn Leu Ser Leu Lys Asn Gly Ser Gly P he Gly Lys Lys Ser Lys
145                 150                 155                 160

Asp Met Ser Thr Glu Arg Asp Phe Phe Met A rg Met Lys Cys Thr Val
                165                 170                 175

Thr Asn Arg Gly Arg Thr Val Asn Leu Lys S er Ala Thr Trp Lys Val
            180                 185                 190

Leu His Cys Thr Gly Gln Val Lys Val Tyr A sn Asn Cys Pro Pro His
        195                 200                 205

Asn Ser Leu Cys Gly Tyr Lys Glu Pro Leu L eu Ser Cys Leu Ile Ile
    210                 215                 220

Met Cys Glu Pro Ile Gln His Pro Ser His M et Asp Ile Pro Leu Asp
225                 230                 235                 240

Ser Lys Thr Phe Leu Ser Arg His Ser Met A sp Met Lys Phe Thr Tyr
                245                 250                 255

Cys Asp Asp Arg Ile Thr Glu Leu Ile Gly T yr His Pro Glu Glu Leu
            260                 265                 270

Leu Gly Arg Ser Ala Tyr Glu Phe Tyr His A la Leu Asp Ser Glu Asn
        275                 280                 285

Met Thr Lys Ser His Gln Asn Leu Cys Thr L ys Gly Gln Val Val Ser

-continued

```
            290                 295                 300
Gly Gln Tyr Arg Met Leu Ala Lys His Gly Gly Tyr Val Trp Leu Glu
305                 310                 315                 320

Thr Gln Gly Thr Val Ile Tyr Asn Pro Arg Asn Leu Gln Pro Gln Cys
                325                 330                 335

Ile Met Cys Val Asn Tyr Val Leu Ser Glu Ile Glu Lys Asn Asp Val
                340                 345                 350

Val Phe Ser Met Asp Gln Thr Glu Ser Leu Phe Lys Pro His Leu Met
                355                 360                 365

Ala Met Asn Ser Ile Phe Asp Ser Ser Gly Lys Gly Ala Val Ser Glu
                370                 375                 380

Lys Ser Asn Phe Leu Phe Thr Lys Leu Lys Glu Glu Pro Glu Glu Leu
385                 390                 395                 400

Ala Gln Leu Ala Pro Thr Pro Gly Asp Ala Ile Ile Ser Leu Asp Phe
                405                 410                 415

Gly Asn Gln Asn Phe Glu Glu Ser Ser Ala Tyr Gly Lys Ala Ile Leu
                420                 425                 430

Pro Pro Ser Gln Pro Trp Ala Thr Glu Leu Arg Ser His Ser Thr Gln
                435                 440                 445

Ser Glu Ala Gly Ser Leu Pro Ala Phe Thr Val Pro Gln Ala Ala Ala
450                 455                 460

Pro Gly Ser Thr Thr Pro Ser Ala Thr Ser Ser Ser Ser Cys Ser
465                 470                 475                 480

Thr Pro Asn Ser Pro Glu Asp Tyr Tyr Thr Ser Leu Asp Asn Asp Leu
                485                 490                 495

Lys Ile Glu Val Ile Glu Lys Leu Phe Ala Met Asp Thr Glu Ala Lys
                500                 505                 510

Asp Gln Cys Ser Thr Gln Thr Asp Phe Asn Glu Leu Asp Leu Glu Thr
                515                 520                 525

Leu Ala Pro Tyr Ile Pro Met Asp Gly Glu Asp Phe Gln Leu Ser Pro
                530                 535                 540

Ile Cys Pro Glu Glu Arg Leu Leu Ala Glu Asn Pro Gln Ser Thr Pro
545                 550                 555                 560

Gln His Cys Phe Ser Ala Met Thr Asn Ile Phe Gln Pro Leu Ala Pro
                565                 570                 575

Val Ala Pro His Ser Pro Phe Leu Leu Asp Lys Phe Gln Gln Gln Leu
                580                 585                 590

Glu Ser Lys Lys Thr Glu Pro Glu His Arg Pro Met Ser Ser Ile Phe
                595                 600                 605

Phe Asp Ala Gly Ser Lys Ala Ser Leu Pro Pro Cys Cys Gly Gln Ala
610                 615                 620

Ser Thr Pro Leu Ser Ser Met Gly Gly Arg Ser Asn Thr Gln Trp Pro
625                 630                 635                 640

Pro Asp Pro Pro Leu His Phe Gly Pro Thr Lys Trp Ala Val Gly Asp
                645                 650                 655

Gln Arg Thr Glu Phe Leu Gly Ala Ala Pro Leu Gly Pro Pro Val Ser
                660                 665                 670

Pro Pro His Val Ser Thr Phe Lys Thr Arg Ser Ala Lys Gly Phe Gly
                675                 680                 685

Ala Arg Gly Pro Asp Val Leu Ser Pro Ala Met Val Ala Leu Ser Asn
                690                 695                 700

Lys Leu Lys Leu Lys Arg Gln Leu Glu Tyr Glu Glu Gln Ala Phe Gln
705                 710                 715                 720
```

```
Asp Leu Ser Gly Gly Asp Pro Gly Gly Ser Thr Ser His Leu Met
                725                 730                 735

Trp Lys Arg Met Lys Asn Leu Arg Gly Gly Ser Cys Pro Leu Met Pro
            740                 745                 750

Asp Lys Pro Leu Ser Ala Asn Val Pro Asn Asp Lys Phe Thr Gln Asn
        755                 760                 765

Pro Met Arg Gly Leu Gly His Pro Leu Arg His Leu Pro Leu Pro Gln
    770                 775                 780

Pro Pro Ser Ala Ile Ser Pro Gly Glu Asn Ser Lys Ser Arg Phe Pro
785                 790                 795                 800

Pro Gln Cys Tyr Ala Thr Gln Tyr Gln Asp Tyr Ser Leu Ser Ser Ala
            805                 810                 815

His Lys Val Ser Gly Met Ala Ser Arg Leu Leu Gly Pro Ser Phe Glu
            820                 825                 830

Ser Tyr Leu Leu Pro Glu Leu Thr Arg Tyr Asp Cys Glu Val Asn Val
            835                 840                 845

Pro Val Leu Gly Ser Ser Thr Leu Leu Gln Gly Gly Asp Leu Leu Arg
        850                 855                 860

Ala Leu Asp Gln Ala Thr
865             870

<210> SEQ ID NO 7
<211> LENGTH: 2818
<212> TYPE: DNA
<213> ORGANISM: Homo sapiens

<400> SEQUENCE: 7
cctgactgcg cggggcgctc gggacctgcg cgcacctcgg accttcacca c ccgcccggg        60 ccgcggggag cggacgaggg ccacagcccc ccacccgcca gggagcccag g tgctcggcg       120 tctgaacgtc tcaaagggcc acagcgacaa tgacagctga caaggagaag a aaaggagta       180 gctcggagag gaggaaggag aagtcccggg atgctgcgcg tgccggcgg a gcaaggaga       240 cggaggtgtt ctatgagctg gcccatgagc tgcctctgcc ccacagtgtg a gctcccatc       300 tggacaaggc ctccatcatg cgactggaaa tcagcttcct gcaacacac a agctcctct       360 cctcagtttg ctctgaaaac gagtccgaag ccgaagctga ccagcagatg g acaacttgt       420 acctgaaagc cttggagggt ttcattgccg tggtgaccca agatggcgac a tgatctttc       480 tgtcagaaaa catcagcaag ttcatgggac ttacacaggt ggagctaaca g gacatagta       540 tctttgactt cactcatccc tgcgaccatg aggagattcg tgagaacctg a gtctcaaaa       600 atggctctgg ttttgggaaa aaagcaaag acatgtccac agagcgggac t tcttcatga       660 ggatgaagtg cacggtcacc aacagaggcc gtactgtcaa cctcaagtca g ccacctgga       720 aggtcttgca ctgcacgggc caggtgaaag tctacaacac tgccctcct c acaatagtc       780 tgtgtggcta caaggagccc ctgctgtcct gcctcatcat catgtgtgaa c caatccagc       840 acccatccca catggacatc cccctggata gcaagacctt cctgagccgc c acagcatgg       900 acatgaagtt cacctactgt gatgacagaa tcacagaact gattggttac c ccctgagg       960 agctgcttgg ccgctcagcc tatgaattct accatgcgct agactccgag a catgacca      1020 agagtcacca gaacttgtgc accaagggtc aggtagtaag tggccagtac c ggatgctcg      1080 caaagcatgg gggctacgtg tggctggaga cccaggggac ggtcatctac a ccctcgca      1140 acctgcagcc ccagtgcatc atgtgtgtca actacgtcct gagtgagatt g agaagaatg      1200
```

-continued

```
acgtggtgtt ctccatggac cagactgaat ccctgttcaa gccccacctg a tggccatga    1260 acagcatctt tgatagcagt ggcaaggggg ctgtgtctga agagtaac t tcctattca    1320 ccaagctaaa ggaggagccc gaggagctgg cccagctggc tcccacccca g gagacgcca    1380 tcatctctct ggatttcggg aatcagaact tcgaggagtc ctcagcctat g gcaaggcca    1440 tcctgccccc gagccagcca tgggccacgg agttgaggag ccacagcacc c agagcgagg    1500 ctgggagcct gcctgccttc accgtgcccc aggcagctgc cccgggcagc a ccacccca    1560 gtgccaccag cagcagcagc agctgctcca cgcccaatag ccctgaagac t attacacat    1620 ctttggataa cgacctgaag attgaagtga ttgagaagct cttcgccatg g acacagagg    1680 ccaaggacca atgcagtacc cagacggatt tcaatgagct ggacttggag a cactggcac    1740 cctatatccc catggacggg gaagacttcc agctaagccc catctgcccc g aggagcggc    1800 tcttggcgga gaacccacag tccaccccc agcactgctt cagtgccatg a caaacatct    1860 tccagccact ggcccctgta gccccgcaca gtcccttcct cctggacaag t ttcagcagc    1920 agctggagag caagaagaca gagcccgagc accggcccat gtcctccatc t tctttgatg    1980 ccggaagcaa agcatccctg ccaccgtgct gtggccaggc cagcaccct c tctcttcca    2040 tggggggcag atccaatacc cagtggcccc cagatccacc attacatttt g ggcccacaa    2100 agtgggccgt cggggatcag cgcacagagt tcttgggagc agcgccgttg g ggcccctg    2160 tctctccacc ccatgtctcc accttcaaga caaggtctgc aaagggtttt g gggctcgag    2220 gcccagacgt gctgagtccg gccatggtag ccctctccaa caagctgaag c tgaagcgac    2280 agctggagta tgaagagcaa gccttccagg acctgagcgg gggggaccca c ctggtggca    2340 gcacctcaca tttgatgtgg aaacggatga agaacctcag gggtgggagc t gccctttga    2400 tgccggacaa gccactgagc gcaaatgtac ccaatgataa gttcacccaa a ccccatga    2460 ggggcctggg ccatcccctg agacatctgc cgctgccaca gcctccatct g ccatcagtc    2520 ccggggagaa cagcaagagc aggttccccc cacagtgcta cgccacccag t accaggact    2580 acagcctgtc gtcagcccac aaggtgtcag gcatggcaag ccggctgctc g ggccctcat    2640 ttgagtccta cctgctgccc gaactgacca gatatgactg tgaggtgaac g tgcccgtgc    2700 tgggaagctc cacgctcctg caaggagggg acctcctcag agccctggac c aggccacct    2760 gagccaggcc ttctacctgg gcagcacctc tgccgacgcc gtcccaccag c ttcaccc    2818
```

```
<210> SEQ ID NO 8
<211> LENGTH: 22
<212> TYPE: DNA
<213> ORGANISM: Artificial sequence
<220> FEATURE:
<223> OTHER INFORMATION: Synthetically generated p rimer

<400> SEQUENCE: 8
gaacttggat gctctttgga aa                                               22

<210> SEQ ID NO 9
<211> LENGTH: 21
<212> TYPE: DNA
<213> ORGANISM: Artificial sequence
<220> FEATURE:
<223> OTHER INFORMATION: Synthetically generated p rimer

<400> SEQUENCE: 9
cacttgctgg catcataagg c                                                21
```

```
<210> SEQ ID NO 10
<211> LENGTH: 21
<212> TYPE: DNA
<213> ORGANISM: Artificial sequence
<220> FEATURE:
<223> OTHER INFORMATION: Synthetically generated p rimer

<400> SEQUENCE: 10
catcatgtgt gagccaatcc a                                              21

<210> SEQ ID NO 11
<211> LENGTH: 21
<212> TYPE: DNA
<213> ORGANISM: Artificial sequence
<220> FEATURE:
<223> OTHER INFORMATION: Synthetically generated p rimer

<400> SEQUENCE: 11
gttgtagatg accgtcccct g                                              21

<210> SEQ ID NO 12
<211> LENGTH: 21
<212> TYPE: DNA
<213> ORGANISM: Artificial sequence
<220> FEATURE:
<223> OTHER INFORMATION: Synthetically generated p rimer

<400> SEQUENCE: 12
tgtactgaga gatgggaacc g                                              21

<210> SEQ ID NO 13
<211> LENGTH: 21
<212> TYPE: DNA
<213> ORGANISM: Artificial sequence
<220> FEATURE:
<223> OTHER INFORMATION: Synthetically generated p rimer

<400> SEQUENCE: 13
cacttgctgg catcataagg c                                              21

<210> SEQ ID NO 14
<211> LENGTH: 20
<212> TYPE: DNA
<213> ORGANISM: Artificial sequence
<220> FEATURE:
<223> OTHER INFORMATION: Synthetically generated p rimer

<400> SEQUENCE: 14
gtgaagacat cgcggggacc                                                20

<210> SEQ ID NO 15
<211> LENGTH: 23
<212> TYPE: DNA
<213> ORGANISM: Artificial sequence
<220> FEATURE:
<223> OTHER INFORMATION: Synthetically generated p rimer

<400> SEQUENCE: 15
gtttgtgcag tattgtagcc agg                                            23

<210> SEQ ID NO 16
<211> LENGTH: 7
<212> TYPE: PRT
<213> ORGANISM: Artificial sequence
<220> FEATURE:
<223> OTHER INFORMATION: Synthetically generated p eptide
```

```
<400> SEQUENCE: 16

Gly Gly Gly Gly Ser Ser Ser
 1               5

<210> SEQ ID NO 17
<211> LENGTH: 101
<212> TYPE: PRT
<213> ORGANISM: Homo sapiens

<400> SEQUENCE: 17

Pro Gly Gly Ser Thr Ser His Leu Met Trp Lys Arg Met Lys Asn Leu
 1               5                  10                  15

Arg Gly Gly Ser Cys Pro Leu Met Pro Asp Lys Pro Leu Ser Ala Asn
            20                  25                  30

Val Pro Asn Asp Lys Phe Thr Gln Asn Pro Met Arg Gly Leu His Pro
        35                  40                  45

Leu Arg His Leu Pro Leu Pro Gln Pro Pro Ser Ala Ile Ser Pro Gly
    50                  55                  60

Glu Asn Ser Lys Ser Arg Phe Pro Pro Gln Cys Tyr Ala Thr Gln Tyr
 65                  70                  75                  80

Gln Asp Tyr Ser Leu Ser Ser Ala His Lys Val Ser Gly Met Ala Ser
                85                  90                  95

Arg Leu Leu Gly Pro
            100

<210> SEQ ID NO 18
<211> LENGTH: 234
<212> TYPE: PRT
<213> ORGANISM: Homo sapiens

<400> SEQUENCE: 18

Asp Pro Pro Leu His Phe Gly Pro Thr Lys Trp Pro Val Gly Asp Gln
 1               5                  10                  15

Ser Ala Glu Ser Leu Gly Ala Leu Pro Val Gly Ser Trp Gln Leu Glu
            20                  25                  30

Leu Pro Ser Ala Pro Leu His Val Ser Met Phe Lys Met Arg Ser Ala
        35                  40                  45

Lys Asp Phe Gly Ala Arg Gly Pro Tyr Met Met Ser Pro Ala Met Ile
    50                  55                  60

Ala Leu Ser Asn Lys Leu Lys Leu Lys Arg Gln Leu Glu Tyr Glu Glu
 65                  70                  75                  80

Gln Ala Phe Gln Asp Thr Ser Gly Gly Asp Pro Pro Gly Thr Ser Ser
                85                  90                  95

Ser His Leu Met Trp Lys Arg Met Lys Ser Leu Met Gly Gly Thr Cys
                100                 105                 110

Pro Leu Met Pro Asp Lys Thr Ile Ser Ala Asn Met Ala Pro Asp Glu
            115                 120                 125

Phe Thr Gln Lys Ser Met Arg Gly Leu Gly Gln Pro Leu Arg His Leu
        130                 135                 140

Pro Pro Pro Gln Pro Pro Ser Thr Arg Ser Ser Gly Glu Asn Ala Lys
145                 150                 155                 160

Thr Gly Phe Pro Pro Gln Cys Tyr Ala Ser Gln Phe Gln Asp Tyr Gly
                165                 170                 175

Pro Pro Gly Ala Gln Lys Val Ser Gly Val Ala Ser Arg Leu Leu Gly
            180                 185                 190

Pro Ser Phe Glu Pro Tyr Leu Leu Pro Glu Leu Thr Arg Tyr Asp Cys
```

Glu Val Asn Val Pro Val Pro Gly Ser Ser Thr Leu Leu Gln Gly Arg
210                 215                 220

Asp Leu Leu Arg Ala Leu Asp Gln Ala Thr
225                 230

<210> SEQ ID NO 19
<211> LENGTH: 602
<212> TYPE: PRT
<213> ORGANISM: Homo sapiens

<400> SEQUENCE: 19

Met Ala Glu Glu Ala Ala Gly Gly Lys Val Leu Arg Glu
1               5               10              15

Glu Asn Gln Cys Ile Ala Pro Val Val Ser Ser Arg Val Ser Pro Gly
                20                  25                  30

Thr Arg Pro Thr Ala Met Gly Ser Phe Ser Ser His Met Thr Glu Phe
            35                  40                  45

Pro Arg Lys Arg Lys Gly Ser Asp Ser Asp Pro Ser Gln Val Glu Asp
        50                  55                  60

Gly Glu His Gln Val Lys Met Lys Ala Phe Arg Glu Ala His Ser Gln
65                  70                  75                  80

Thr Glu Lys Arg Arg Arg Asp Lys Met Asn Ala Asn Leu Ile Glu Glu Leu
                85                  90                  95

Ser Ala Met Ile Pro Gln Cys Asn Pro Met Ala Arg Lys Leu Asp Lys
                100                 105                 110

Leu Thr Val Leu Arg Met Ala Val Gln His Leu Arg Ser Leu Lys Gly
            115                 120                 125

Leu Thr Asn Ser Tyr Val Gly Ser Asn Tyr Arg Pro Ser Phe Leu Gln
130                 135                 140

Asp Asn Glu Leu Arg His Leu Ile Leu Lys Thr Ala Glu Gly Phe Leu
145                 150                 155                 160

Phe Val Val Gly Cys Glu Arg Gly Lys Ile Leu Phe Val Ser Lys Ser
                165                 170                 175

Val Ser Lys Ile Leu Asn Tyr Asp Gln Ala Ser Leu Thr Gly Gln Ser
            180                 185                 190

Leu Phe Asp Phe Leu His Pro Lys Asp Val Ala Lys Val Lys Glu Gln
        195                 200                 205

Leu Ser Ser Phe Asp Ile Ser Pro Arg Glu Lys Leu Ile Asp Ala Lys
    210                 215                 220

Thr Gly Leu Gln Val His Ser Asn Leu His Ala Gly Arg Thr Arg Val
225                 230                 235                 240

Tyr Ser Gly Ser Arg Arg Ser Phe Phe Cys Arg Ile Lys Ser Cys Lys
                245                 250                 255

Ile Ser Val Lys Glu Glu His Gly Cys Leu Pro Asn Ser Lys Lys Lys
            260                 265                 270

Glu His Arg Lys Phe Tyr Thr Ile His Cys Thr Gly Tyr Leu Arg Ser
        275                 280                 285

Trp Pro Pro Asn Ile Val Gly Met Glu Glu Arg Asn Ser Lys Lys
    290                 295                 300

Asp Asn Ser Asn Phe Thr Cys Leu Val Ala Ile Gly Arg Leu Gln Pro
305                 310                 315                 320

Tyr Ile Val Pro Gln Asn Ser Gly Glu Ile Asn Val Lys Pro Thr Glu
                325                 330                 335

-continued

```
Phe Ile Thr Arg Phe Ala Val Asn Gly Lys P he Val Tyr Val Asp Gln
            340                 345                 350
Arg Ala Thr Ala Ile Leu Gly Tyr Leu Pro G ln Glu Leu Leu Gly Thr
            355                 360                 365
Ser Cys Tyr Glu Tyr Phe His Gln Asp Asp H is Asn Asn Leu Thr Asp
            370                 375                 380
Lys His Lys Ala Val Leu Gln Ser Lys Glu L ys Ile Leu Thr Asp Ser
385                 390                 395                 400
Tyr Lys Phe Arg Ala Lys Asp Gly Ser Phe V al Thr Leu Lys Ser Gln
                405                 410                 415
Trp Phe Ser Phe Thr Asn Pro Trp Thr Lys G lu Leu Glu Tyr Ile Val
                420                 425                 430
Ser Val Asn Thr Leu Val Leu Gly His Ser G lu Pro Gly Glu Ala Ser
                435                 440                 445
Phe Leu Pro Cys Ser Ser Gln Ser Ser Glu G lu Ser Ser Arg Gln Ser
            450                 455                 460
Cys Met Ser Val Pro Gly Met Ser Thr Gly T hr Val Leu Gly Ala Gly
465                 470                 475                 480
Ser Ile Gly Thr Asp Ile Ala Asn Glu Ile L eu Asp Leu Gln Arg Leu
                485                 490                 495
Gln Ser Ser Tyr Leu Asp Asp Ser Ser P ro Thr Gly Leu Met Lys
                500                 505                 510
Asp Thr His Thr Val Asn Cys Arg Ser Met S er Asn Lys Glu Leu Phe
            515                 520                 525
Pro Pro Ser Pro Ser Glu Met Gly Glu Leu G lu Ala Thr Arg Gln Asn
            530                 535                 540
Gln Ser Thr Val Ala Val His Ser His Glu P ro Leu Leu Ser Asp Gly
545                 550                 555                 560
Ala Gln Leu Asp Phe Asp Ala Leu Cys Asp A sn Asp Asp Thr Ala Met
                565                 570                 575
Ala Ala Phe Met Asn Tyr Leu Glu Ala Glu G ly Gly Leu Gly Asp Pro
                580                 585                 590
Gly Asp Phe Ser Asp Ile Gln Trp Thr Leu
                595                 600
```

<210> SEQ ID NO 20
<211> LENGTH: 6792
<212> TYPE: DNA
<213> ORGANISM: Homo sapiens

<400> SEQUENCE: 20

```
ctccagtccg catgctcagt agctgctgcc ggccgggctg cggggcggcg t ccgctgcgc      60
gcctacgggc tgcggtggcg gccgccgcgg cacccggcag ggcccgccag t ccccgcttc     120
cctgctccag agccgccgcc tgggccgggg cagggcgggc ccggggctcc t ccatgctgc     180
cagccgccgg gctgcggagc cgaccaagtg gctcctgcga tggcggcgga a gaggaggct     240
gcggcgggag gtaaagtgtt gagagaggag aaccagtgca ttgctcctgt g gtttccagc     300
cgcgtgagtc caggacaag accaacagct atggggtctt tcagctcaca c atgacagag     360
tttccacgaa aacgcaaagg aagtgattca gacccatccc aagtggaaga t ggtgaacac     420
caagttaaaa tgaaggcctt cagagaagct catagccaaa ctgaaaagcg g aggagagat     480
aaaatgaata acctgattga agaactgtct gcaatgatcc ctcagtgcaa c cccatggcg     540
cgtaaactgg acaaacttac agttttaaga atggctgttc aacacttgag a tctttaaaa     600
```

-continued

| | |
|---|---|
| ggcttgacaa attcttatgt gggaagtaat tatagaccat catttcttca g gataatgag | 660 |
| ctcagacatt taatccttaa gactgcagaa ggcttcttat tgtggttgg a tgtgaaaga | 720 |
| ggaaaaattc tcttcgtttc taagtcagtc tccaaaatac ttaattatga t caggctagt | 780 |
| ttgactggac aaagcttatt tgacttctta catccaaaag atgttgccaa a gtaaaggaa | 840 |
| caactttctt cttttgatat tcaccaagaa gaaaagctaa tagatgccaa a actggtttg | 900 |
| caagttcaca gtaatctcca cgctggaagg acacgtgtgt attctggctc a agacgatct | 960 |
| tttttctgtc ggataaagag ttgtaaaatc tctgtcaaag aagagcatgg a tgcttaccc | 1020 |
| aactcaaaga agaaagagca cagaaaattc tatactatcc attgcactgg t tacttgaga | 1080 |
| agctggcctc caaatattgt tggaatggaa gaagaaagga acagtaagaa a gacaacagt | 1140 |
| aattttacct gccttgtggc cattggaaga ttacagccat atattgttcc a cagaacagt | 1200 |
| ggagagatta atgtgaaacc aactgaattt ataacccggt ttgcagtgaa t ggaaaattt | 1260 |
| gtctatgtag atcaaagggc aacagcgatt ttaggatatc tgcctcagga a cttttggga | 1320 |
| acttcttgtt atgaatattt tcatcaagat gaccacaata atttgactga c aagcacaaa | 1380 |
| gcagttctac agagtaagga gaaaatactt acagattcct acaaattcag a gcaaaagat | 1440 |
| ggctcttttg taactttaaa aagccaatgg tttagtttca caaatccttg g acaaaagaa | 1500 |
| ctggaatata ttgtatctgt caacacttta gttttgggac atagtgagcc t ggagaagca | 1560 |
| tcatttttac cttgtagctc tcaatcatca gaagaatcct ctagacagtc c tgtatgagt | 1620 |
| gtacctggaa tgtctactgg aacagtactt ggtgctggta gtattggaac a gatattgca | 1680 |
| aatgaaattc tggatttaca gaggttacag tcttcttcat accttgatga t tcgagtcca | 1740 |
| acaggtttaa tgaaagatac tcatactgta aactgcagga gtatgtcaaa t aaggagttg | 1800 |
| tttccaccaa gtccttctga atgggggag ctagaggcta ccaggcaaaa c cagagtact | 1860 |
| gttgctgtcc acagccatga gccactcctc agtgatggtg cacagttgga t ttcgatgcc | 1920 |
| ctatgtgaca atgatgacac agccatggct gcatttatga attacttaga a gcagagggg | 1980 |
| ggcctgggag accctgggga cttcagtgac atccagtgga ccctctagcc t ttgatttt | 2040 |
| aactccaaaa atgagaaaca ttttaaagca ttatttacga aaaaactgtc t caactattc | 2100 |
| ttaagtactg tattgatatt gtttgtatct tttattaatg ttctaccact t tttatagat | 2160 |
| ttgcatcttc ctgtcacagg gatgtgggga aatacgtttt cctcccaaga g aaccaagtt | 2220 |
| tattatagac tcctttattc agtgaaatgg cttataatcc actagttgcc a tatttttgc | 2280 |
| taaaatattt ctaaccaaga atactactta catattgttt tggctttgtt t tattttga | 2340 |
| tgcagttttt tttagttgag gtaatgtaat atattgatgt tttcctttgt g tctaagatt | 2400 |
| gatttataat agtaggtttg tataatttgg aacattttcc atgccttgcg a atttcctta | 2460 |
| attgaggata gggcttacac actttaagaa aacagtgagt acttgaacat t taagggac | 2520 |
| agtgcaattt atagtcataa tcacattgaa tactgtattt gatctttgga g acttaggca | 2580 |
| agcacagagc tggatatttt atgctcagtt gagcacttta agatgaattt t aagtgagat | 2640 |
| gatttcttgc ttaaaactca gaaagtcaaa agagtttcag ctttccttac a gaaaaggaa | 2700 |
| ggatcttggg ccctagatct tgggattaa cctctgcata taagatttac t cttaatagg | 2760 |
| ccagacgtgg tgctcacgcc tgtaatccca gtactttggg aggctgagac g gcagatca | 2820 |
| cttgaggtca ggagttcaag accagcctgg ccaatatggt gaaacccgt t tctactaaa | 2880 |
| aatacaaaaa aaattccca ggcactcact cttgaggtaa ctaaccaact c ccacgataa | 2940 |
| tgacagtcca ttcatgagcg caaggcctc atgacctaat ggcacacacc t gtaatccca | 3000 |

```
actgcttggg aggctgaggc gagaggattg cttgaacctg ggaggcagag g ttgcagtga    3060 gccgagatcg caccactgca ctccagtctg ggcaacagag tgagacttca t ctcaaaaaa    3120 agtaaaaaaa aagatttaat ataatcactg aagatctcta ttatagatag a ttaggtttt    3180 tgacattgga aacatactta gggatagatt tgtcctaaag gaaaaaagta g gcccgggca    3240 gattaaatgt cttgtgtaaa gtcacacatt aaattcagtc acacattaaa t tcatagagt    3300 tttaaatgtt taatgtatat aaaccagttt ctttatacac atttgggaaa a cattggtct    3360 cacagattaa atgattaact aactgaccca ggaactagtt gtagctttct a agtaattag    3420 gcaattacag ttattgcctg taaccaaagg taataaaaca aaatgacaag t acatgttta    3480 aaattatgag gcaatgagaa ataatttaaa aaccaatttt ctagttataa t ttaaaattt    3540 ggagagcatt tttaacagta attaatccag aggtggctca aattgagtat a agaattaag    3600 attatttaaa atactgcatg tctaccttct cggggatcat actttataac a ctttctgct    3660 tcagtagctc ttcatagctt gccaagtatg ctcccatatt ttctctctcg t gcctcgcaa    3720 atgaaagtca gataggctgg gaactcatgg ggcagccctc agacttcaat g tgggcttca    3780 aatccagttt cctgttctat atggtgctac atctttccag aaaatttccc t cagagcccc    3840 tcgccaaaac aaagcattat tttgaccctg catgctattt ctttagctgt a ggtgataga    3900 ttagaacttc tgtcagacat gttaatgaca acataccaa cagacaataa c caaagcaaa    3960 tgtttccttc aagtgtgaaa tgtgcagggg ctcgtgggca aggatgtatt g gcacactgt    4020 cctcttgaac tgatagtgtc ccagcaatgt tggaggttgg caccattcct g gtccgacac    4080 ttgaggacct gagagacatc aggtttagaa tgagccaaag aaatcctaca a gatggggag    4140 aattggtgtg cagcagccta agtgttatag ttaagtctaa agaagtatga a agatcccct    4200 gtgttctcta aattgagcag aggggcctgc ctaccaatat cacttttag g ggactgaac    4260 cattgcaggt tagacttggc ttccaaagag tctgcctaag ccaggggtgg c agggtaggc    4320 catcatagct ggatggcctc aaaagcagat ggggcagac ttgccctcgt g atgccagga    4380 tttgagaggc agagtttcta gagggagacc agtgctgcct ctcacagtgg c agtttttc    4440 tctttgcaag aggaggggct gttcaattcc atagaccagt gggcagatag c cagttgaat    4500 actctgtgca tggtttgatc ctttattagt tcgctctaat attttctgt a gatccttt    4560 gtcctggact caaaatctaa tccatgcatt gtatgatacc gtagctctcc t aaggtttgt    4620 gtttccttca aaatgtttta gttttcttca actaaatttg attttttgctg t tagaagtga    4680 catattttta tggtatacac tatgttcctt ttttctactg cgagtcaatt t tttgaattt    4740 tcgtgagaaa gaatatatct acaaattgca cgaaagtatc ataaaaacag t actctagag    4800 cagcgctgtc aatagaaat ataatctgag ccacatgtat aattttattt t cttctagcc    4860 acattaaaga agtaaaaaga tacaagtaga actaattta atgttttaat t cagtatatc    4920 caaaatatca tttgaacatg taattaatat aaaattatta atgtgatatt t tacattctt    4980 ttggtaatac tagtcttcaa aatctggtat gtatcttaca ttgatagcac a tctcacttt    5040 gtactagcca cattgcaagt gctcagtagc cacatgtggc tagtggctac t gcactggac    5100 agcacagttc taggttccac cctaacaccc aagtcctgtg gattagaatc c cagaatcag    5160 agctggaagt aaacatagag atcaaacctc cttttaaaaa tgaggacgct g aggcacaga    5220 gtttaaatgg cttgcatgag gtcatacagc taaattcagc ctcaacaggg t cttctgatt    5280 ccaggcactc ttcccactcc actacattac tgtagtggta attcttaggg t taaaaaaag    5340
```

-continued

```
tgtagagtag gccgggcgca gtggctcatg cctgtaatcc cagcactttg g gaggccgaa    5400 gtgggcggat cacgaggtca ggagatcgag accatcctgg ccaacatggt g aaacccgt    5460 ctctactgaa aatacaaagc aaaattagcc aggtgtggtg gcgggcgcct g tggtcccag   5520 ctgctctgga ggctgaggca gaatggcgtg aacccaggag gcagagatgg c agtgagcca   5580 agatcgcgcc actgcacccc agcctgggcg acagagcgag actccatctc a aaaaaaaaa   5640 aaaaaaaaa aagaaaagaa aagaaaagtc tagagaacat tatattaagt g gttattatt   5700 gaagtagacc aaagtttata ccataaggat attttccctt aaataccatg t ttgaagaac   5760 aattatttat tgatccttga atctgtaaga tcaaataaca agtctctatc c atgttacca   5820 aatttaacct tttgaaaata ataaacttta aaatatcaga tgtgttatta c aggatgata   5880 cttggaatca agtgaaatga gttatatggt catcactaaa tttagaaatc t attgtgaaa   5940 caaagacaaa caggaaagta cagaatagag acttttagta aataaatgga a tttaaaaga   6000 aagtgtttat ttacagtgtc acgacagaaa aggatgtctt tgttgtcata g tctttgagg   6060 gatctccgta aaatctgggg cacaggtaca agaaatagcc aatatttagt t cccagacca   6120 tgtttagtag tgtccagttt cagatcatgc tgccaagagg tatctccccc t caggtgggt   6180 catcactgag ccctggaatt ggagactcat acttgcccag cacaatgtta c gggcagaca   6240 ggccgacatc tatgattagc tagaagccat aaagaaaagc tgctaagtgg c cactaggtg   6300 ccacttttct gttttttgtaa tgctttcatt agcagatctt ttttttccaa g ctccatggg   6360 gcctatgaga ggcattatg attttttgtgc ctacaataag tcagcctgtc t ggtgtgagt   6420 tgttttatga gaaatgcttt ccaagggagg tctaggaaga tcctgacaca t aagaacttt   6480 ggcttagaga gctttccagg tgtagtgcca ataaaaactg acctggaaag a aaacctgcc   6540 cagcacggaa catgctttct gaactcactt gagagtgtat ggtgtatgtc a cttctcata   6600 tattcttgag tttagatttg tcttttatac aattttttagc tcttttccag t tcacttgtg   6660 ctcgtctgta tattggtatt tttaaatttt tgtggtaaat aatgaaaaga g tgaaattat   6720 attttataat tactcatttg tagtttttttt ttttaattta ataaacttcc t ccaaaaagt   6780 gctcccttaa aa                                                        6792
```

```
<210> SEQ ID NO 21
<211> LENGTH: 626
<212> TYPE: PRT
<213> ORGANISM: Homo sapiens

<400> SEQUENCE: 21

Met Ala Asp Gln Arg Met Asp Ile Ser Ser T hr Ile Ser Asp Phe Met
  1               5                  10                  15

Ser Pro Gly Pro Thr Asp Leu Leu Ser Ser S er Leu Gly Thr Ser Gly
                 20                  25                  30

Val Asp Cys Asn Arg Lys Arg Lys Gly Ser S er Thr Asp Tyr Gln Glu
             35                  40                  45

Ser Met Asp Thr Asp Lys Asp Pro His G ly Arg Leu Glu Tyr Thr
         50                  55                  60

Glu His Gln Gly Arg Ile Lys Asn Ala Arg G lu Ala His Ser Gln Ile
 65                  70                  75                  80

Glu Lys Arg Arg Arg Asp Lys Met Asn Ser P he Ile Asp Glu Leu Ala
                 85                  90                  95

Ser Leu Val Pro Thr Cys Asn Ala Met Ser A rg Lys Leu Asp Lys Leu
                100                 105                 110
```

```
Thr Val Leu Arg Met Ala Val Gln His Met Arg Thr Leu Arg Gly Ala
        115                 120                 125

Thr Asn Pro Tyr Thr Glu Ala Asn Tyr Lys Pro Thr Phe Leu Ser Asp
        130                 135                 140

Asp Glu Lys His Leu Ile Leu Arg Ala Ala Asp Gly Phe Leu Phe
145                 150                 155                 160

Val Val Gly Cys Asp Arg Gly Lys Ile Leu Phe Val Ser Glu Ser Val
                165                 170                 175

Phe Lys Ile Leu Asn Tyr Ser Gln Asn Asp Leu Ile Gly Gln Ser Leu
                180                 185                 190

Phe Asp Tyr Leu His Pro Lys Asp Ile Ala Lys Val Lys Glu Gln Leu
                195                 200                 205

Ser Ser Ser Asp Thr Ala Pro Arg Glu Ala Leu Ile Asp Ala Lys Thr
        210                 215                 220

Gly Leu Pro Val Lys Thr Asp Ile Thr Pro Gly Pro Ser Arg Leu Cys
225                 230                 235                 240

Ser Gly Ala Arg Arg Ser Phe Phe Cys Arg Met Lys Cys Asn Arg Pro
                245                 250                 255

Ser Val Lys Val Glu Asp Lys Asp Phe Pro Ser Thr Cys Ser Lys Lys
                260                 265                 270

Lys Ala Asp Arg Lys Ser Phe Cys Thr Ile His Ser Thr Gly Tyr Leu
        275                 280                 285

Lys Ser Trp Pro Pro Thr Lys Met Gly Leu Asp Glu Asp Asn Glu Pro
        290                 295                 300

Asp Asn Glu Gly Cys Asn Leu Ser Cys Leu Val Ala Ile Gly Arg Leu
305                 310                 315                 320

His Ser His Val Val Pro Gln Pro Val Asn Gly Glu Ile Arg Val Lys
                325                 330                 335

Ser Met Glu Tyr Val Ser Arg His Ala Ile Asp Gly Lys Phe Val Phe
                340                 345                 350

Val Asp Gln Arg Ala Thr Ala Ile Leu Ala Tyr Leu Pro Gln Glu Leu
                355                 360                 365

Leu Gly Thr Ser Cys Tyr Glu Tyr Phe His Gln Asp Asp Ile Gly His
        370                 375                 380

Leu Ala Glu Cys His Arg Gln Val Leu Gln Thr Arg Glu Lys Ile Thr
385                 390                 395                 400

Thr Asn Cys Tyr Lys Phe Lys Ile Lys Asp Gly Ser Phe Ile Thr Leu
                405                 410                 415

Arg Ser Arg Trp Phe Ser Phe Met Asn Pro Trp Thr Lys Glu Val Glu
                420                 425                 430

Tyr Ile Val Ser Thr Asn Thr Val Val Leu Ala Asn Val Leu Glu Gly
        435                 440                 445

Gly Asp Pro Thr Phe Pro Gln Leu Thr Ala Ser Pro His Ser Met Asp
450                 455                 460

Ser Met Leu Pro Ser Gly Glu Gly Pro Lys Arg Thr His Pro Thr
465                 470                 475                 480

Val Pro Gly Ile Pro Gly Gly Thr Arg Ala Gly Ala Gly Lys Ile Gly
                485                 490                 495

Arg Met Ile Ala Glu Ile Met Glu Ile His Arg Ile Arg Gly Ser
                500                 505                 510

Ser Pro Ser Ser Cys Gly Ser Ser Pro Leu Asn Ile Thr Ser Thr Pro
        515                 520                 525

Pro Pro Asp Ala Ser Ser Pro Gly Gly Lys Lys Ile Leu Asn Gly Gly
```

```
            530                 535                 540
Thr Pro Asp Ile Pro Ser Ser Gly Leu Leu S er Gly Gln Ala Gln Glu
545                 550                 555                 560

Asn Pro Gly Tyr Pro Tyr Ser Asp Ser Ser S er Ile Leu Gly Glu Asn
                565                 570                 575

Pro His Ile Gly Ile Asp Met Ile Asp Asn A sp Gln Gly Ser Ser Ser
                580                 585                 590

Pro Ser Asn Asp Glu Ala Ala Met Ala Val I le Met Ser Leu Leu Glu
                595                 600                 605

Ala Asp Ala Gly Leu Gly Pro Val Asp P he Ser Asp Leu Pro Trp
            610                 615                 620

Pro Leu
625

<210> SEQ ID NO 22
<211> LENGTH: 789
<212> TYPE: PRT
<213> ORGANISM: Homo sapiens

<400> SEQUENCE: 22

Met Ala Ala Thr Thr Ala Asn Pro Glu Met T hr Ser Asp Val Pro Ser
 1               5                  10                  15

Leu Gly Pro Ala Ile Ala Ser Gly Asn Ser G ly Pro Gly Ile Gln Gly
                20                  25                  30

Gly Gly Ala Ile Val Gln Arg Ala Ile Lys A rg Arg Pro Gly Leu Asp
            35                  40                  45

Phe Asp Asp Asp Gly Glu Gly Asn Ser Lys P he Leu Arg Cys Asp Asp
    50                  55                  60

Asp Gln Met Ser Asn Asp Lys Glu Arg Phe A la Arg Ser Asp Asp Glu
65                  70                  75                  80

Gln Ser Ser Ala Asp Lys Glu Arg Leu Ala A rg Glu Asn His Ser Glu
                85                  90                  95

Ile Glu Arg Arg Arg Asn Lys Met Thr A la Tyr Ile Thr Glu Leu
                100                 105                 110

Ser Asp Met Val Pro Thr Cys Ser Ala Leu A la Arg Lys Pro Asp Lys
            115                 120                 125

Leu Thr Ile Leu Arg Met Ala Val Ser His M et Lys Ser Leu Arg Gly
130                 135                 140

Thr Gly Asn Thr Ser Thr Asp Gly Ser Tyr L ys Pro Ser Phe Leu Thr
145                 150                 155                 160

Asp Gln Glu Leu Lys His Leu Ile Leu Glu A la Ala Asp Gly Phe Leu
                165                 170                 175

Phe Ile Val Ser Cys Glu Thr Gly Arg Val V al Tyr Val Ser Asp Ser
            180                 185                 190

Val Thr Pro Val Leu Asn Gln Pro Gln Ser G lu Trp Phe Gly Ser Thr
        195                 200                 205

Leu Tyr Asp Gln Val His Pro Asp Asp Val A sp Lys Leu Arg Glu Gln
    210                 215                 220

Leu Ser Thr Ser Glu Asn Ala Leu Thr Gly A rg Ile Leu Asp Leu Lys
225                 230                 235                 240

Thr Gly Thr Val Lys Lys Glu Gly Gln Gln S er Ser Met Arg Met Cys
                245                 250                 255

Met Gly Ser Arg Arg Ser Phe Ile Cys Arg M et Arg Cys Gly Ser Ser
            260                 265                 270
```

```
Ser Val Asp Pro Val Ser Val Asn Arg Leu Ser Phe Val Arg Asn Arg
        275                 280                 285

Cys Arg Asn Gly Leu Gly Ser Val Lys Asp Gly Glu Pro His Phe Val
    290                 295                 300

Val Val His Cys Thr Gly Tyr Ile Lys Ala Trp Pro Pro Ala Gly Val
305                 310                 315                 320

Ser Leu Pro Asp Asp Pro Glu Ala Gly Gln Gly Ser Lys Phe Cys
                325                 330                 335

Leu Val Ala Ile Gly Arg Leu Gln Val Thr Ser Ser Pro Asn Cys Thr
                340                 345                 350

Asp Met Ser Asn Val Cys Gln Pro Thr Glu Phe Ile Ser Arg His Asn
        355                 360                 365

Ile Glu Gly Ile Phe Thr Phe Val Asp His Arg Cys Val Ala Thr Val
    370                 375                 380

Gly Tyr Gln Pro Gln Glu Leu Leu Gly Lys Asn Ile Val Glu Phe Cys
385                 390                 395                 400

His Pro Glu Asp Gln Gln Leu Leu Arg Asp Ser Phe Gln Gln Val Val
                405                 410                 415

Lys Leu Lys Gly Gln Val Leu Ser Val Met Phe Arg Phe Arg Ser Lys
                420                 425                 430

Asn Gln Glu Trp Leu Trp Met Arg Thr Ser Ser Phe Thr Phe Gln Asn
        435                 440                 445

Pro Tyr Ser Asp Glu Ile Glu Tyr Ile Ile Cys Thr Asn Thr Asn Val
    450                 455                 460

Lys Asn Ser Ser Gln Glu Pro Arg Pro Thr Leu Ser Asn Thr Ile Gln
465                 470                 475                 480

Arg Pro Gln Leu Gly Pro Thr Ala Asn Leu Pro Leu Glu Met Gly Ser
                485                 490                 495

Gly Gln Leu Ala Pro Arg Gln Gln Gln Gln Thr Glu Leu Asp Met
        500                 505                 510

Val Pro Gly Arg Asp Gly Leu Ala Ser Tyr Asn His Ser Gln Val Val
        515                 520                 525

Gln Pro Val Thr Thr Thr Gly Pro Glu His Ser Lys Pro Leu Glu Lys
    530                 535                 540

Ser Asp Gly Leu Phe Ala Gln Asp Arg Asp Pro Arg Phe Ser Glu Ile
545                 550                 555                 560

Tyr His Asn Ile Asn Ala Asp Gln Ser Lys Gly Ile Ser Ser Ser Thr
                565                 570                 575

Val Pro Ala Thr Gln Gln Leu Phe Ser Gln Gly Asn Thr Phe Pro Pro
        580                 585                 590

Thr Pro Arg Pro Ala Glu Asn Phe Arg Asn Ser Gly Leu Ala Pro Pro
    595                 600                 605

Val Thr Ile Val Gln Pro Ser Ala Ser Ala Gly Gln Met Leu Ala Gln
        610                 615                 620

Ile Ser Arg His Ser Asn Pro Thr Gln Gly Ala Thr Pro Thr Trp Thr
625                 630                 635                 640

Pro Thr Thr Arg Ser Gly Phe Ser Ala Gln Gln Val Ala Thr Gln Ala
                645                 650                 655

Thr Ala Lys Thr Arg Thr Ser Gln Phe Gly Val Gly Ser Phe Gln Thr
                660                 665                 670

Pro Ser Ser Phe Ser Ser Met Ser Leu Pro Gly Ala Pro Thr Ala Ser
                675                 680                 685

Pro Gly Ala Ala Ala Tyr Pro Ser Leu Thr Asn Arg Gly Ser Asn Phe
```

-continued

```
            690                 695                 700
Ala Pro Glu Thr Gly Gln Thr Ala Gly Gln Phe Gln Thr Arg Thr Ala
705                 710                 715                 720

Glu Gly Val Gly Val Trp Pro Gln Trp Gln Gly Gln Gln Pro His His
                725                 730                 735

Arg Ser Ser Ser Glu Gln His Val Gln Gln Pro Pro Ala Gln Gln
            740                 745                 750

Pro Gly Gln Pro Glu Val Phe Gln Glu Met Leu Ser Met Leu Gly Asp
            755                 760                 765

Gln Ser Asn Ser Tyr Asn Asn Glu Glu Phe Pro Asp Leu Thr Met Phe
    770                 775                 780

Pro Pro Phe Ser Glu
785
```

Other embodiments are within the following claims.

What is claimed is:

1. A nucleic acid encoding a deletion mutant of an EPAS1 polypeptide which deletion mutant binds to the nucleotide sequence of SEQ ID NO:1, wherein said EPAS1 polypeptide consists of the amino acid sequence of SEQ ID NO:6 and wherein said deletion mutant comprises the amino acid sequence of SEQ ID NO:4 and a functional deletion in a transactivation domain, said transactivation domain consisting of the amino acid sequence of SEQ ID NO:2.

2. The nucleic acid of claim 1, wherein said nucleic acid encodes an EPAS1 polypeptide lacking amino acids 486–639 of SEQ ID NO:6.

3. The nucleic acid of claim 1, wherein said EPAS1 polypeptide comprises the amino acid sequence of SEQ ID NO:4.

4. The nucleic acid of claim 1 wherein said nucleic acid comprises the nucleotide sequence of SEQ ID NO:5.

5. A method of inhibiting expression of an angiogenic factor in a mammalian vascular endothelial cell in vitro, comprising contacting said mammalian vascular endotheliar cell with the nucleic acid of claim 1, wherein the promoter of said angiogenic factor comprises the nucleotide sequence disclosed in SEQ ID NO1.

6. The method of claim 5, wherein said nucleic acid encodes an EPAS1 polypeptide comprising the amino acid sequence of SEQ ID NO:4.

7. The method of claim 5, wherein said nucleic acid comprises the nucleotide sequence of SEQ ID NO:5.

* * * * *